(12) United States Patent
Chan Chun Kong et al.

(10) Patent No.: US 7,709,642 B2
(45) Date of Patent: May 4, 2010

(54) SPIROHYDANTOIN COMPOUNDS AND METHODS FOR THE MODULATION OF CHEMOKINE RECEPTOR ACTIVITY

(75) Inventors: Laval Chan Chun Kong, Kirkland (CA); Christophe Moinet, Montreal (CA); Louis Vaillancourt, Mascouche (CA); Monica Bubenik, Montreal (CA)

(73) Assignee: Virochem Pharma, Inc., Laval, Quebec (CA)

( * ) Notice: Subject to any disclaimer, the term of this patent is extended or adjusted under 35 U.S.C. 154(b) by 1049 days.

(21) Appl. No.: 11/159,406

(22) Filed: Jun. 23, 2005

(65) Prior Publication Data
US 2006/0014769 A1    Jan. 19, 2006

Related U.S. Application Data

(60) Provisional application No. 60/582,540, filed on Jun. 25, 2004.

(51) Int. Cl.
| | |
|---|---|
| *A01N 43/42* | (2006.01) |
| *A61K 31/44* | (2006.01) |
| *C07D 401/00* | (2006.01) |
| *C07D 451/00* | (2006.01) |
| *C07D 453/00* | (2006.01) |
| *C07D 455/00* | (2006.01) |
| *C07D 471/00* | (2006.01) |

(52) U.S. Cl. ......................................... 546/17; 514/278
(58) Field of Classification Search ........................ None
See application file for complete search history.

(56) References Cited

FOREIGN PATENT DOCUMENTS

| CA | 2389034 A1 | 5/2001 |
|---|---|---|
| EP | 0 094 343 A1 | 4/1983 |
| WO | WO 97/11940 A1 | 4/1997 |
| WO | WO 2005/007656 A1 | 1/2005 |
| WO | WO 2005/023809 A1 | 3/2005 |
| WO | WO 2005/023810 A1 | 3/2005 |
| WO | WO 2006/060918 A1 | 6/2006 |
| WO | WO 2006/060919 A1 | 6/2006 |

OTHER PUBLICATIONS

Kazmierski et. al., Current medicinal Chemistry (2005), 4:133-152.*
Kazmierski et al. (Bioorganic & Medicinal Chemistry 2003; 11: 2663-2676).*
Cichoki, www.about.com, all about HIV Tropism, updated Dec. 14, 2007.*
International Search Report for PCT/CA2005/000999 dated Oct. 24, 2005.
International Preliminary Report on Patentability for PCT/CA2005/000999 issued Dec. 28, 2006.
Written Opinion of the International Searching Authority for International Application No. PCT/CA2005/000999 mailed Oct. 24, 2005.

* cited by examiner

*Primary Examiner*—Frederick Krass
*Assistant Examiner*—Marcos Sznaidman
(74) *Attorney, Agent, or Firm*—Millen, White, Zelano & Branigan, P.C.

(57) ABSTRACT

Novel compounds represented by formula (I):

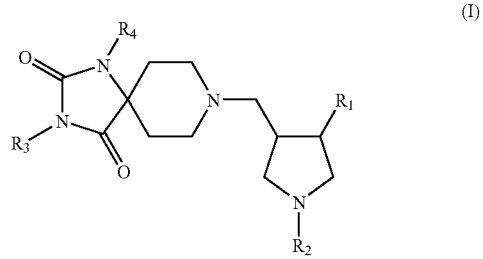

wherein $R_1$, $R_2$, $R_3$ and $R_4$ are as defined herein, and pharmaceutically acceptable salts, hydrates and solvates thereof, are useful for the modulation of CCR5 chemokine receptor activity.

44 Claims, No Drawings

SPIROHYDANTOIN COMPOUNDS AND METHODS FOR THE MODULATION OF CHEMOKINE RECEPTOR ACTIVITY

This application claims the benefit of U.S. provisional application 60/582,540 filed Jun. 25, 2004, the entire disclosure of which is herein incorporated by reference.

FIELD OF THE INVENTION

The present invention relates to novel spirohydantoin compounds and a method of modulating chemokine receptor activity using these compounds. The present invention is also directed to novel spirohydantoin compounds which are useful in the prevention or treatment of diseases associated with the modulation of CCR5 chemokine receptor activity. The present invention is further directed to a method of blocking cellular entry of HIV in a subject and to compositions using these compounds.

BACKGROUND OF THE INVENTION

Chemokines are chemotactic cytokines that are released by a wide variety of cells to attract macrophages, T cells, eosinophils, basophils and neutrophils to sites of inflammation and they also play a role in the maturation of cells of the immune system. Chemokines play an important role in immune and inflammatory responses in various diseases and disorders, including asthma, rhinitis and allergic diseases, as well as autoimmune pathologies such as rheumatoid arthritis and atherosclerosis. Chemokines are small 70 to 80 amino acid proteins with well-characterized three-dimensional structures, usually stabilized by two disulfide bridges. They are divided into four families on the basis of pattern of conserved cysteine residues. Chemokine receptors have been designated such as, CCR1, CCR2, CCR2A, CCR2B, CCR3, CCR4, CCR5, CCR6, CCR7, CCR8, CCR9, CCR10, CXCR1, CXCR2, CXCR3, and CXCR4 and therefore agents which modulate these receptors may be useful in the prevention and treatment of diseases as mentioned above.

One of them, the C—C chemokines family, includes potent chemoattractants of monocytes and lymphocytes such as RANTES (Regulated on Activation, Normal T Expressed and Secreted), eotaxin, MIP-1α and MIP-1β (Macrophage Inflammatory Proteins) and human monocyte chemotactic proteins 1-3 (MCP-1, MCP-2 and MCP-3). More specifically, C—C chemokine receptor 5 (CCR5), a β-chemokine receptor with a seven-transmembrane-protein structure, was found to serve as a coreceptor for non-syncytium-inducing or macrophage-tropic HIV-1 (R5 viruses). It was also established that CCR5 is the principal chemokine receptor required for the entry of HIV into the cell during primary infection. Therefore, interfering with the interaction between the viral receptor CCR5 and HIV can block HIV entry into the cell. It would therefore be useful to provide novel compounds which are modulators of chemokine receptor activity.

SUMMARY OF THE INVENTION

In one aspect, the present invention provides novel compounds represented by formula (I):

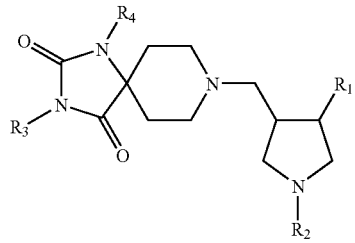

or a pharmaceutically acceptable salt, hydrate or solvate thereof, wherein $R_1$ is H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{7-12}$ aralkyl or optionally substituted 4-10 membered heteroaralkyl;

$R_2$ is H,

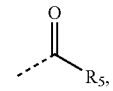

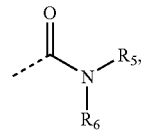

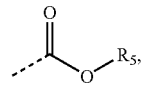

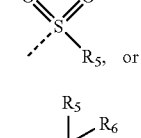

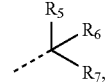

$R_3$ and $R_4$ are each chosen independently H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{7-12}$ aralkyl or optionally substituted 4-10 membered heteroaralkyl;

$R_5$ is H, optionally substituted $C_{1-10}$ alkyl, optionally substituted $C_{2-10}$ alkenyl, optionally substituted $C_{2-10}$ alkynyl, optionally substituted $C_{6-12}$ aryl, optionally substituted 3 to 10 membered heterocycle, optionally substituted $C_{7-12}$ aralkyl or optionally substituted 4 to 10 membered heteroaralkyl;

$R_6$ is H, optionally substituted $C_{1-10}$ alkyl, optionally substituted $C_{2-10}$ alkenyl, or optionally substituted $C_{2-10}$ alkynyl; or $R_5$ and $R_6$ can be taken together to form an optionally substituted 3 to 10 membered heterocycle; and $R_7$ is H, optionally substituted $C_{1-10}$ alkyl, optionally substituted $C_{2-10}$ alkenyl, or optionally substituted $C_{2-10}$ alkynyl.

In another aspect, there is provided a method of modulating chemokine receptor activity in a subject comprising administering to the subject an effective amount of a compound of formula (I) or composition of the invention.

In still another aspect, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In still another aspect, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject comprising administering to the subject in need thereof an effective amount of a compound of formula (I) or composition of the invention to block HIV from cellular entry in said subject.

In still another aspect, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In another aspect, there is provided a pharmaceutical formulation comprising a compound of the invention in combination with a pharmaceutically acceptable carrier or excipient.

In another aspect of the invention is the use of a compound according to formula (I), for the manufacture of a medicament for the prevention or treatment of diseases associated with the modulation of chemokine receptor activity.

DETAILED DESCRIPTION OF THE INVENTION

In one embodiment, compounds of the present invention comprise those wherein the following embodiments are present, either independently or in combination.

In one embodiment, the present invention provides novel compounds represented by formula (I):

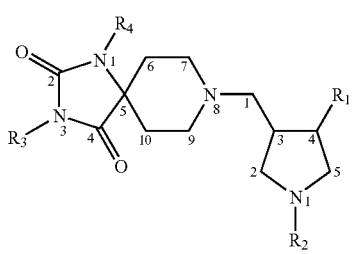

(I)

or a pharmaceutically acceptable salt, hydrate or solvate thereof wherein $R_1$, $R_2$, $R_3$ and $R_4$ are defined above.

In a further embodiment, $R_1$ is optionally substituted $C_{6-12}$ aryl.

In a further embodiment, $R_1$ is optionally substituted phenyl.

In a further embodiment, $R_1$ is unsubstituted phenyl or phenyl substituted by one or more substituent chosen from methyl, F, Cl and Br.

In a further embodiment, $R_5$ is H, optionally substituted $C_{1-10}$ alkyl, optionally substituted $C_{2-10}$ alkenyl, optionally substituted $C_{2-10}$ alkynyl, optionally substituted $C_{6-12}$ aryl, or optionally substituted $C_{7-12}$ aralkyl.

In a further embodiment, $R_5$ is H, optionally substituted $C_{1-10}$ alkyl, optionally substituted $C_{6-12}$ aryl, or optionally substituted $C_{7-12}$ aralkyl.

In a further embodiment, $R_5$ is H or optionally substituted $C_{1-6}$ alkyl.

In a further embodiment, $R_5$ is unsubstituted $C_{1-6}$ alkyl or $C_{1-6}$ alkyl substituted by one or more substituent chosen from —$OCH_3$, F, Cl and Br.

In a further embodiment, $R_5$ is methyl, ethyl, propyl, isopropyl, cyclopropyl, butyl, tert-butyl, $CH_2$-tert-butyl cyclobutyl, pentyl, cyclopentyl, hexyl, cyclohexyl, heptyl, cycloheptyl, $CH_2$-cyclopropyl, $CH_2$-cyclobutyl, $CH_2$-cyclopentyl, or $CH_2$-cyclohexyl.

In a further embodiment, $R_5$ is optionally substituted $C_{6-12}$ aryl.

In a further embodiment, $R_5$ is unsubstituted $C_{6-12}$ aryl or $C_{6-12}$ aryl substituted by one or more substituent chosen from —$OCH_3$, F, Cl and Br.

In a further embodiment, $R_5$ is optionally substituted phenyl.

In a further embodiment, $R_5$ is unsubstituted phenyl or phenyl substituted by one or more substituent chosen from —$OCH_3$, F, Cl and Br.

In a further embodiment, $R_5$ is optionally substituted 3 to 10 membered heterocycle.

In a further embodiment, $R_5$ is pyridine, furan or thiophene

In a further embodiment, $R_2$ is:

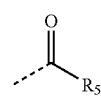

(II)

wherein:

$R_5$ is methyl;

$R_5$ is ethyl;

$R_5$ is isopropyl;

$R_5$ is cyclopropyl;

$R_5$ is cyclobutyl;

$R_5$ is cyclopentyl;

$R_5$ is cyclohexyl;

$R_5$ is cycloheptyl;

$R_5$ is $CH_2$-cyclopropyl;

$R_5$ is $CH_2$-cyclobutyl;

$R_5$ is $CH_2$-cyclopentyl; or $R_5$ is $CH_2$-cyclohexyl;

in each case optionally substituted.

In a further embodiment, $R_2$ is:

(II)

wherein:
$R_5$ is phenyl, optionally substituted;
$R_5$ is phenyl substituted with methyl;
$R_5$ is phenyl substituted with at least one methyl;
$R_5$ is phenyl substituted with a halogen;
$R_5$ is phenyl substituted with at least one halogen;
$R_5$ is phenyl substituted with Cl;
$R_5$ is phenyl substituted with Br;
$R_5$ is phenyl substituted with F;
$R_5$ is phenyl substituted with at least one Cl; or
$R_5$ is phenyl substituted with methoxy.
In a further embodiment, $R_2$ is:

(II)

wherein:
$R_5$ is benzyl, optionally substituted;
$R_5$ is benzyl substituted with methyl;
$R_5$ is benzyl substituted with at least one methyl;
$R_5$ is benzyl substituted with a halogen;
$R_5$ is benzyl substituted with at least one halogen;
$R_5$ is benzyl substituted with Cl;
$R_5$ is benzyl substituted with Br;
$R_5$ is benzyl substituted with F;
$R_5$ is benzyl substituted with at least one Cl; or
$R_5$ is benzyl substituted with methoxy;
In a further embodiment, $R_2$ is:

(II)

wherein:
$R_5$ is pyridine;
$R_5$ is furan; or
$R_5$ is thiophene;

in each case optionally substituted.
In a further embodiment, $R_2$ is:

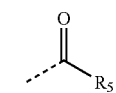
(III)

wherein $R_5$ is phenyl, optionally substituted, and $R_6$ is H.
In a further embodiment, $R_2$ is:

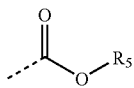
(IV)

wherein $R_5$ is tert-butyl.
In a further embodiment, $R_2$ is:

(V)

wherein $R_5$ is phenyl, optionally substituted.
In a further embodiment, $R_2$ is:

(VI)

wherein:
$R_5$ is phenyl, or cyclohexyl, in each case optionally substituted.
$R_6$ and $R_7$ are H.
In one embodiment, $R_3$ is optionally substituted $C_{7-12}$ aralkyl or optionally substituted 4 to 10 membered heteroaralkyl.
In a further embodiment, $R_3$ is optionally substituted $C_{7-12}$ aralkyl.
In a further embodiment, $R_3$ is optionally substituted 4 to 10 membered heteroaralkyl.
In further embodiments:
$R_3$ is benzyl, optionally substituted;
$R_3$ is benzyl substituted with a halogen;
$R_3$ is benzyl substituted with Br;
$R_3$ is benzyl substituted with F;
$R_3$ is benzyl substituted with Cl;
$R_3$ is benzyl substituted with at least one halogen;
$R_3$ is benzyl substituted with a $C_{1-3}$ alkoxy;
$R_3$ is benzyl substituted with methoxy;
$R_3$ is benzyl substituted with $SO_2C_{1-3}$alkyl;
$R_3$ is benzyl substituted with methanesulfonyl;
$R_3$ is benzyl optionally substituted in the para (p) position;
$R_3$ is pyridinyl-methyl, optionally substituted.
In one embodiment, $R_4$ is chosen from H or optionally substituted $C_{1-6}$ alkyl.
In one embodiment, $R_4$ is unsubstituted $C_{1-6}$ alkyl or $C_{1-6}$ alkyl substituted by one or more substituent chosen from OMe, Cl and Br.
In one embodiment, $R_4$ is methyl, ethyl, propyl, pentyl, cyclopentyl, hexyl, cyclohexyl, CH2-cyclopropyl, CH2-cyclobutyl, CH2-cyclopentyl, or CH2-cyclohexyl.
In one embodiment, $R_4$ is H.
In one embodiment, $R_4$ is methyl.
The compounds of the present inventions have asymmetric centers. For example, the C-3 and C-4 positions. As two optical isomers can independently be obtained from each asymmetric center, it is intended that all the possible optical isomers and diastereomers in mixtures and as pure or partially purified compounds are included in this invention.

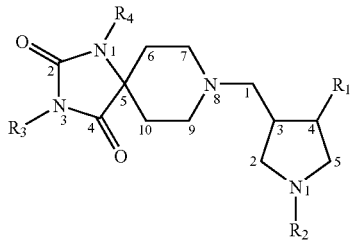

In one embodiment, the compounds of the present invention are in the form of the (3R,4R)-diastereomer;

In one embodiment, the compounds of the present invention are in the form of the (3S,4R)-diastereomer;

In one embodiment, the compounds of the present invention are in the form of the (3R, 4S)-diastereomer;

In one embodiment, the compounds of the present invention are in the form of the (3S,4S)-diastereomer.

In one embodiment, the compounds of the present invention are the (+) diastereoisomers having an optical purity in excess of 99%.

In one embodiment, the compounds of the present invention are the (+) diastereoisomers having an optical purity in excess of 95%.

In one embodiment, the compounds of the present invention are the (+) diastereoisomers having an optical purity in excess of 90%.

In one embodiment, the compounds of the present invention are the (−) diastereoisomers having an optical purity in excess of 99%.

In one embodiment, the compounds of the present invention are the (−) diastereoisomers having an optical purity in excess of 95%.

In one embodiment, the compounds of the present invention are the (−) diastereoisomers having an optical purity in excess of 90%.

In one embodiment the compounds of the present invention comprise diastereomers where C-3 and C-4 substituents are in the trans configuration.

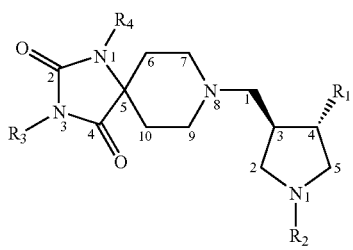

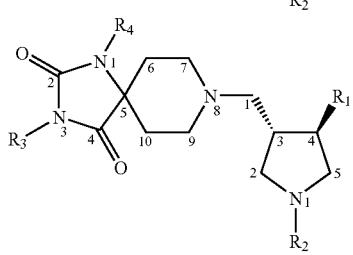

In one embodiment the compounds of the present invention comprise diastereomers where C-3 and C-4 substituents are in the cis configuration.

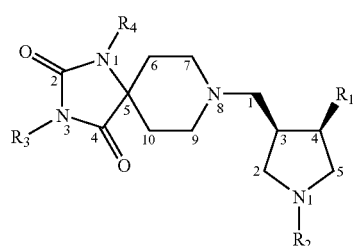

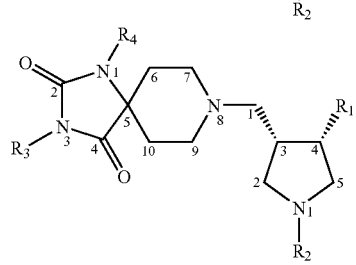

In one embodiment, there is provided a method of modulating chemokine receptor activity in a subject comprising administering to the subject an effective amount of a compound of formula (I) or composition of the invention.

In another embodiment, there is provided a method for the prevention or treatment of diseases associated with the modulation of chemokine receptor activity in a subject in need of such treatment comprising administering to the subject a therapeutically effective amount of a compound of formula (I) or composition of the invention.

In a further embodiment, there is provided a method for prevention or treatment of certain inflammatory diseases, immunoregulatory diseases, organ transplantation reactions and in the prevention and treatment of infectious diseases such as HIV infections in a subject in need of such treatment comprising administering to the subject a therapeutically effective amount of a compound of formula (I) or composition of the invention.

In another embodiment, there is provided a method for the prevention or treatment of diseases associated with the modulation of CCR5 chemokine receptor activity in a subject in need of such treatment comprising administering to the subject a therapeutically effective amount of a compound of formula (I) or composition of the invention.

In still another aspect, there is provided a method for blocking cellular entry of HIV in a subject in need thereof comprising administering to the subject an effective amount of a compound of formula (I) to block HIV from cellular entry in said subject.

In still another aspect, there is provided a method for prevention or treatment of HIV infections in a subject in need of such treatment comprising administering to the subject a therapeutically effective amount of a compound of formula (I) or composition of the invention.

In still another aspect, there is provided a method for delaying the onset of AIDS or treating AIDS in a subject in need of such treatment comprising administering to the subject a therapeutically effective amount of a compound of formula (I) or composition of the invention.

In a further embodiment, there is provided a method for the prevention or treatment of diseases associated with the modulation of chemokine receptor activity in a subject in need of such treatment comprising administering to the subject a pharmaceutical combination comprising at least one compound of formula (I) and at least one further therapeutic agent.

In a further embodiment, there is provided a method for the prevention or treatment of diseases associated with the modulation of CCR5 chemokine receptor activity in a subject in need of such treatment comprising administering to the subject a pharmaceutical combination comprising at least one compound of formula (I) and at least one further therapeutic agent.

In still another aspect, there is provided a method for blocking cellular entry of HIV in a subject or for the prevention or treatment of HIV infections in a subject in need of such treatment comprising administering to the subject a pharmaceutical combination comprising at least one compound of formula (I) and at least one further therapeutic agent.

In still another aspect, there is provided a method for delaying the onset of AIDS or treating AIDS in a subject in need of such treatment comprising administering to the subject a pharmaceutical combination comprising at least one compound of formula (I) and at least one further therapeutic agent.

In another embodiment, there is provided a combination useful for the prevention or treatment of diseases associated with the modulation of chemokine receptor activity which is a therapeutically effective amount of a compound of formula (I) and therapeutically effective amount of at least one further therapeutic agent.

In one embodiment, combinations of the present invention comprise those wherein the following embodiments are present, either independently or in combination.

In a further embodiment, the pharmaceutical combinations of this invention may contain at least one further therapeutic agent chosen from an agent used in inflammatory diseases, immunoregulatory diseases and in organ transplantation reactions.

In another embodiment, the pharmaceutical combination of this invention may contain at least one further therapeutic agent which is an antiviral agent.

In one embodiment, the pharmaceutical combination of this invention may contain at least one further antiviral agent which is chosen from nucleoside and nucleotide analog reverse transcriptase inhibitors, non-nucleoside reverse transcriptase inhibitors, protease inhibitors, attachment and fusion inhibitors, integrase inhibitors or maturation inhibitors.

In one embodiment, the pharmaceutical combinations of this invention may contain at least one other antiviral agent which is a nucleoside and nucleotide analog reverse transcriptase inhibitors chosen from 3TC (lamivudine, Epivir®), AZT (zidovudine, Retrovir®), Emtricitabine (Coviracil®, formerly FTC), d4T (2',3'-dideoxy-2',3'-didehydro-thymidine, stavudine and Zerit®), tenofovir (Viread®), 2',3'-dideoxyinosine (ddI, didanosine, Videx®), 2',3'-dideoxycytidine (ddC, zalcitabine, Hivid®), Combivir® (AZT/3TC or zidovudine/lamivudine combination), Trivizir® (AZT/3TC/abacavir or zidovudine/lamivudine/abacavir combination), abacavir (1592U89, Ziagen®), SPD-754, ACH-126,443 (Beta-L-Fd4C), Alovudine (MIV-310), DAPD (amdoxovir), Racivir, 9-[(2-hydroxymethyl)-1,3-dioxolan-4-yl]guanine or 2-amino-9-[(2-hydroxymethyl)-1,3-dioxolan-4-yl]adenine.

In another embodiment, the pharmaceutical combination of this invention may contain at least one other antiviral agent which is a non-nucleoside reverse transcriptase inhibitor chosen from Nevirapine (Viramune®, NVP, BI-RG-587), delavirdine (Rescriptor®, DLV), efavirenz (DMP 266, Sustiva®), (+)-Calanolide A, Capravirine (AG1549, formerly S-1153), DPC083, MIV-150, TMC120, TMC125 or BHAP (delavirdine), calanolides or L-697,661 (2-Pyridinone 3benzoxazolMeNH derivative).

In another embodiment, the pharmaceutical combination of this invention may contain at least one other antiviral agent which is a protease inhibitor chosen from nelfinavir (Viracept®, NFV), amprenavir (141W94, Agenerase®), indinavir (MK-639, IDV, Crixivan®), saquinavir (Invirase®, Fortovase®, SQV), ritonavir (Norvir®, RTV), lopinavir (ABT-378, Kaletra®), Atazanavir (BMS232632), mozenavir (DMP-450), fosamprenavir (GW433908), RO033-4649, Tipranavir (PNU-140690), TMC114 or VX-385.

In another embodiment, the pharmaceutical combination of this invention may contain at least one other antiviral agent which is an attachment and fusion inhibitor chosen from T-20 (enfuvirtide, Fuzeon®), T-1249, Schering C (SCH-C), Schering D (SCH-D), FP21399, PRO-140, PRO 542, PRO 452, TNX-355, AK602, TAK-220, UK-427,857 or soluble CD4, CD4 fragments, CD4-hybrid molecules, BMS-806 and BMS-488043.

In another embodiment, the pharmaceutical combination of this invention may contain at least one other antiviral agent which is an integrase inhibitor chosen from S-1360, L-870, 810, L-870,812 or C-2507.

In another embodiment, the pharmaceutical combination of this invention may contain at least one other antiviral agent which is a maturation inhibitor and is PA-457.

In another embodiment, the pharmaceutical combination of this invention may contain at least one other antiviral agent which is a zinc finger inhibitor and is azodicarbonamide (ADA).

In another embodiment, the pharmaceutical combination of this invention may contain at least one other antiviral agent which is an antisense drug and is HGTV43.

In another embodiment, the pharmaceutical combination of this invention may contain at least one other antiviral agent which is an immunomodulator, immune stimulator or cytokine chosen from interleukin-2 (IL-2, Aldesleukin, Proleukin), granulocyte macrophage colony stimulating factor (GM-CSF), erythropoietin, Multikine, Ampligen, thymomodulin, thymopentin, foscarnet, HE2000, Reticulose, Murabutide, Resveratrol, HRG214, HIV-1 Immunogen (Remune) or EP HIV-1090.

In another embodiment, the pharmaceutical combination of this invention may contain at least one other antiviral agent chosen from 2',3'-dideoxyadenosine, 3'-deoxythymidine, 2',3'-dideoxy-2',3'-didehydrocytidine and ribavirin; acyclic nucleosides such as acyclovir, ganciclovir; interferons such as alpha-, beta- and gamma-interferon; glucuronation inhibitors such as probenecid; or TIBO drugs, HEPT, TSAO derivatives.

The combinations referred to above may conveniently be presented for use in the form of a pharmaceutical formulation and thus pharmaceutical formulations comprising a combination as defined above together with a pharmaceutically acceptable carrier thereof comprises a further aspect of the invention.

The individual components of such combinations may be administered either sequentially or simultaneously in separate or combined pharmaceutical formulations.

In a further embodiment, the said compound of formula (I) and said therapeutic agent are administered sequentially.

In a further embodiment, the said compound of formula (I) and said therapeutic agent are administered simultaneously.

In one embodiment, the present invention further provides a pharmaceutical composition comprising at least one compound having the formula (I) or pharmaceutically acceptable salts or pharmaceutically acceptable hydrates or pharmaceutically acceptable solvates thereof and at least one pharmaceutically acceptable carrier or excipient.

In another embodiment, the invention provides the use of a compound having the formula (I) for the manufacture of a medicament for prevention and treatment of diseases associated with the modulation of CCR5 chemokine receptor activity in a host comprising administering a therapeutically effective amount of a compound of formula (I).

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety having 1 to 10 carbon atoms, e.g., 1 to 6 carbon atoms, which is optionally substituted. For example, the alkyl group can be substituted by halogen, nitro, hydroxyl, $SO_3H$, $SO_3-C_{1-6}$ alkyl, $PO_3H_2$, $PO_3H-C_{1-6}$ alkyl, $PO_3H-C_{6-12}$ aryl, $PO_3(C_{1-6}$ alkyl$)_2$, $PO_3(C_{6-12}$ aryl$)_2$, $CONH_2$, $CONH-C_{1-6}$ alkyl, $CONH-C_{6-12}$ aryl, $CON(C_{1-6}$ alkyl$)_2$, $CON(C_{6-12}$ aryl$)_2$, $NHCO-C_{1-6}$ alkyl, $NHCO-C_{6-12}$ aryl, COOH, $COO-C_{1-6}$ alkyl, $S-C_{1-6}$ alkyl, $O-C_{1-6}$ alkyl, $O-C_{2-6}$ alkenyl, $O-C_{2-6}$ alkynyl, amino, $NH-C_{1-6}$ alkyl, $NH-C_{6-12}$ aryl, $N(C_{1-6}$ alkyl$)_2$, $N(C_{6-12}$ aryl$)_2$, $C_{6-12}$ aryl, and/or $C_{3-10}$ heterocycle.

The term alkyl is also meant to include alkyls which have both a straight or branched portion and a cyclic portion, e.g., cyclopropylmethyl, cyclobutylmethyl, cyclopentylmethyl, and $CH_2$-cyclohexylmethyl.

The term alkyl is also meant to include alkyls in which one or more hydrogen atom is replaced by a halogen, i.e. an alkylhalide. Examples include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl.

The term "alkenyl" refers to alkyl groups may have one or more double bonds in the chain. The term "alkynyl" refers to alkyl groups may have one or more triple bonds in their chain. Suitable substituents for the alkenyl and alkynyl groups include those substituents listed above for the alkyl groups.

Examples of alkyl, alkenyl and alkynyl include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cycloheptyl, cyclohexenyl, cyclohexdienyl and cyclohexyl.

The term "alkoxy" represents an alkyl which is covalently bonded to the adjacent atom through an oxygen atom, wherein the alkyl portion can be optionally substituted as described above. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy and neohexyloxy.

The term "alkylamino" represents an alkyl which is covalently bonded to the adjacent atom through a nitrogen atom and may be monoalkylamino or dialkylamino, wherein the alkyl groups may be the same or different, and each alkyl portion can be optionally substituted as described above. Examples include but are not limited to methylamino, dimethylamino, ethylamino, diethylamino, methylethylamino, propylamino, isopropylamino, butylamino, isobutylamino, sec-butylamino, tert-butylamino, pentylamino, isopentylamino, neopentylamino, tert-pentylamino, hexylamino, isohexylamino and neohexylamino.

The term "alkyloxycarbonyl", represents an alkoxy group which is covalently bonded to the adjacent atom through carbonyl (C=O), wherein the alkyl portion can be optionally substituted as described above. Examples include but are not limited to methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, tert-pentyloxycarbonyl, hexyloxycarbonyl, isohexyloxycarbonyl and neohexyloxycarbonyl.

The term "amidino" represents $-C(=NR_8)NR_9R_{10}$ wherein $R_8$, $R_9$ and $R_{10}$ are each independently selected from H, $C_{1-6}$ alkyl, $C_{6-12}$ aryl or $C_{7-12}$ aralkyl, or $R_9$ and $R_{10}$ are taken together with the nitrogen to which they are attached to form a 3 to 10 membered heterocycle.

The term "amido" represents $-CONH_2$, $-CONHR_{11}$ and $-CONR_{11}R_{12}$ wherein $R_{11}$ and $R_{12}$ are each independently selected from $C_{1-6}$ alkyl, $C_{6-12}$ aryl, 3 to 10 membered heterocycle or $C_{7-12}$ aralkyl, or $R_{11}$ and $R_{12}$ are taken together with the nitrogen to which they are attached to form a 3 to 10 membered heterocycle.

The term "amino" represents a derivative of ammonia obtained by substituting one or more hydrogen atom and include $-NH_2$, $-NHR_{13}$ and $-NR_{13}R_{14}$, wherein $R_{13}$ and $R_{14}$ are each independently selected from $C_{1-6}$ alkyl, $C_{6-12}$ aryl or $C_{7-12}$ aralkyl, or $R_{13}$ and $R_{14}$ are taken together with the nitrogen to which they are attached to form a 3 to 10 membered heterocycle.

The term "aryl" represents a carbocyclic moiety containing at least one benzenoid-type ring (i.e. it may be monocyclic or polycyclic), and which may be optionally substituted with one or more substituents. For example, the aryl group can be substituted by halogen, nitro, hydroxyl, $SO_3H$, $SO_3-C_{1-6}$ alkyl, $PO_3H_2$, $PO_3H-C_{1-6}$ alkyl, $PO_3H-C_{6-12}$ aryl, $PO_3(C_{1-6}$ alkyl$)_2$, $PO_3(C_{6-12}$ aryl$)_2$, $CONH_2$, $CONH-C_{1-6}$ alkyl, $CONH-C_{6-12}$ aryl, $CON(C_{1-6}$ alkyl$)_2$, $CON(C_{6-12}$ aryl$)_2$, $NHCO-C_{1-6}$ alkyl, $NHCO-C_{6-12}$ aryl, COOH, $COO-C_{1-6}$ alkyl, $S-C_{1-6}$ alkyl, $O-C_{1-6}$ alkyl, $O-C_{2-6}$ alkenyl, $O-C_{2-6}$ alkynyl, amino, $NH-C_{1-6}$ alkyl, $NH-C_{6-12}$ aryl, $N(C_{1-6}$ alkyl$)_2$, $N(C_{6-12}$ aryl$)_2$, $C_{6-12}$ aryl, and/or $C_{3-10}$ heterocycle.

Examples of aryl include but are not limited to phenyl, tolyl, dimethylphenyl, aminophenyl, anilinyl, naphthyl, anthryl, phenanthryl or biphenyl.

The term "aralkyl" represents an aryl group attached to the adjacent atom by a $C_{1-6}$alkyl, wherein the alkyl and aryl portions can each, independently, be optionally substituted as described above. Examples include but are not limited to benzyl, benzhydryl, trityl, phenethyl, 3-phenylpropyl, 2-phenylpropyl, 4-phenylbutyl and naphthylmethyl.

The term "aralkyloxy" represents an aralkyl which is covalently bonded to the adjacent atom through an oxygen atom, wherein the alkyl and aryl portions can each, independently, be optionally substituted as described above. Examples include but are not limited to benzyloxy, benzhydryloxy, trityloxy, phenethyloxy, 3-phenylpropyloxy, 2-phenylpropyloxy, 4-phenylbutyloxy and naphthylmethoxy.

The term "aryloxy" represents an aryl which is covalently bonded to the adjacent atom through an oxygen atom, wherein the aryl portion can be optionally substituted as described above. Examples include but are not limited to phenoxy and naphthyloxy.

The term "guanidino" represents —$NR_{15}C(=NR_{16})NR_{17}R_{18}$ wherein $R_{15}$, $R_{16}$, $R_{17}$ and $R_{18}$ are each independently selected from H, $C_{1-6}$ alkyl, $C_{6-12}$ aryl or $C_{7-12}$ aralkyl, or $R_{17}$ and $R_{18}$ are taken together with the nitrogen to which they are attached to form a 3 to 10 membered heterocycle.

The term "halogen" is specifically a fluoride atom, chloride atom, bromide atom or iodide atom.

The term "heterocycle" represents an optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, the heterocycle group can be substituted by halogen, nitro, hydroxyl, $SO_3H$, $SO_3$—$C_{1-6}$ alkyl, $PO_3H_2$, $PO_3H$—$C_{1-6}$ alkyl, $PO_3H$—$C_{6-12}$ aryl, $PO_3(C_{1-6}$ alkyl$)_2$, $PO_3(C_{6-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$ aryl, COOH, COO—$C_{1-6}$ alkyl, S—$C_{1-6}$ alkyl, O—$C_{1-6}$ alkyl, O—$C_{2-6}$ alkenyl, O—$C_{2-6}$ alkynyl, amino, NH—$C_{1-6}$ alkyl, NH—$C_{6-12}$ aryl, N($C_{1-6}$ alkyl$)_2$, N($C_{6-12}$ aryl$)_2$, $C_{6-12}$ aryl, and/or $C_{3-10}$ heterocycle. Examples of heterocycles include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

The term "heteroaralkyl" represents a heterocycle group attached to the adjacent atom by a $C_{1-6}$ alkyl, wherein the alkyl and heterocycle portions can each, independently, be optionally substituted as described above.

The term "independently" means that a substituent can be the same or a different definition for each item.

The term "optionally substituted" represents one or more halogen, amino, amidino, amido, azido, cyano, guanidino, hydroxyl, nitro, nitroso, urea, $OS(O)_2R_{19}$ (wherein $R_{19}$ is selected from $C_{1-6}$ alkyl, $C_{6-12}$ aryl or 3 to 10 membered heterocycle), $OS(O)_2OR_{20}$ (wherein $R_{20}$ is selected from H, $C_{1-6}$ alkyl, $C_{6-12}$ aryl or 3 to 10 membered heterocycle), $S(O)_2OR_{21}$ (wherein $R_{21}$ is selected from H, $C_{1-6}$ alkyl, $C_{6-12}$ aryl or 3 to 10 membered heterocycle), $S(O)_{0-2}R_{22}$ (wherein $R_{22}$ is selected from H, $C_{1-6}$ alkyl, $C_{6-12}$ aryl or 3 to 10 membered heterocycle), $OP(O)OR_{23}OR_{24}$, $P(O)OR_{23}OR_{24}$ (wherein $R_{23}$ and $R_{24}$ are each independently selected from H or $C_{1-6}$ alkyl), $C_{1-6}$alkyl, $C_{7-12}$aralkyl, $C_{6-12}$ aryl, $C_{1-6}$alkoxy, $C_{6-12}$aralkyloxy, $C_{6-12}$aryloxy, 3 to 10 membered heterocycle, $C(O)R_{25}$ (wherein $R_{25}$ is selected from H, $C_{1-6}$ alkyl, $C_{6-12}$ aryl or 3 to 10 membered heterocycle), $C(O)OR_{26}$ (wherein $R_{26}$ is selected from H, $C_{1-6}$ alkyl, $C_{6-12}$ aryl, $C_{7-12}$ aralkyl or 3 to 10 membered heterocycle) $NR_{27}C(O)R_{28}$ (wherein $R_{27}$ is H or $C_{1-6}$alkyl and $R_{28}$ is selected from H, $C_{1-6}$alkyl, $C_{6-12}$ aryl, $C_{7-12}$aralkyl or 3 to 10 membered heterocycle, or $R_{27}$ and $R_{28}$ are taken together with the atoms to which they are attached to form a 3 to 10 membered heterocycle), $CONR_{27}R_{28}$, $CONR_{27}R_{28}$, $SO_2NR_{29}R_{30}$ (wherein $R_{29}$ and $R_{30}$ are each independently selected from the group consisting of H, $C_{1-6}$ alkyl, $C_{6-12}$ aryl, 3 to 10 membered heterocycle and $C_{7-12}$ aralkyl), $NR_{29}SO_2R_{30}$, or $C(R_{31})NR_{32}$ (wherein $R_{31}$ and $R_{32}$ are each independently selected from the group consisting of H, $C_{1-6}$ alkyl, or $C_{6-12}$ aryl) or $C(R_{31})NOR_{32}$.

The term "urea" represents —$N(R_{31})CONR_{32}R_{33}$ wherein $R_{31}$ is H or $C_{1-6}$ alkyl and wherein $R_{32}$ and $R_{33}$ are each independently selected from the group consisting of H, $C_{1-6}$ alkyl, $C_{6-12}$ aryl, 3 to 10 membered heterocycle and $C_{7-12}$ aralkyl, or $R_{32}$ and $R_{33}$ are taken together with the nitrogen to which they are attached to form a 3 to 10 membered heterocycle.

"Oxidation levels": When there is a sulfur atom present, the sulfur atom can be at different oxidation levels, i.e. S, SO or $SO_2$. All such oxidation levels are within the scope of the present invention. When there is a nitrogen atom present, the nitrogen atom can be at different oxidation levels, i.e. N or NO. All such oxidation levels are within the scope of the present invention.

It will be appreciated that the compounds in accordance with the present invention can contain one or more chiral centers. The compounds in accordance with the present invention may thus exist in the form of two different optical isomers, that is (+) or (−) enantiomers or in the form of different diastereoisomers. All such enantiomers, diastereoisomers and mixtures thereof, including racemic or other ratio mixtures of individual enantiomers and diastereoisomers, are included within the scope of the invention. The single diastereoisomers can be obtained by methods well known to those of ordinary skill in the art, such as HPLC, crystallization and chromatography. The single enantiomer can be obtained by methods well known to those of ordinary skill in the art, such as chiral HPLC, enzymatic resolution and chiral auxiliary derivatization.

The optical purity is numerically equivalent to the "enantiomeric excess". The term "enantiomeric excess" is defined in percentage (%) value as follows: [mole fraction (major enantiomer)−mole fraction (minor enantiomer)]×100. An example of enantiomeric excess of 99% represents a ratio of 99.5% of one enantiomer and 0.5% of the opposite enantiomer.

There is also provided "pharmaceutically acceptable hydrates" of the compounds of the present invention. "Hydrates" exist when the compound of the invention incorporates water. The hydrate may contain one or more molecule of water per molecule of compound of the invention. Illustrative non-limiting examples include monohydrate, dihydrate, trihydrate and tetrahydrate. The hydrate may contain one or more molecule of compound of the invention per molecule of water. An illustrative non-limiting example includes semihydrate. In one embodiment, the water may be held in the crystal in various ways and thus, the water molecules may occupy lattice positions in the crystal, or they may form bonds with salts of the compounds as described herein. The hydrate must be "acceptable" in the sense of not being deleterious to the recipient thereof. The hydration may be assessed by methods known in the art such as Loss on Drying techniques (LOD) and Karl Fisher titration.

There is also provided "pharmaceutically acceptable salts" of the compounds of the present invention. By the term "pharmaceutically acceptable salts" of compounds are meant those derived from pharmaceutically acceptable inorganic and organic acids and bases. Examples of suitable acids include but are not limited to hydrochloric, hydrobromic, sulphuric, nitric, perchloric, fumaric, maleic, phosphoric, glycollic, lactic, salicylic, succinic, toleune-p-sulphonic, tartaric, acetic, trifluoroacetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal, alkaline earth metal or ammonium salts. The salt(s) must be "acceptable" in the sense of not being deleterious to the recipient thereof. Non-limiting examples of such salts known by those of ordinary skill in the art include without limitation calcium, potassium, sodium, choline, ethylenediamine, tromethamine, arginine, glycinelycine, lycine, magnesium and meglumine.

There is also provided a "pharmaceutically acceptable solvates" of the compounds of the present invention. The term "solvate" means that the compound of the invention incorporates one or more pharmaceutically acceptable solvent. The solvate may contain one or more molecule of solvent per molecule of compound of the invention or may contain one or more molecule of compound of the invention per molecule of solvent. In one embodiment, the solvent may be held in the crystal in various ways and thus, the solvent molecule may occupy lattice positions in the crystal, or they may form bonds with salts of the compounds as described herein. The solvate (s) must be "acceptable" in the sense of not being deleterious to the recipient thereof. The salvation may be assessed by methods known in the art such as Loss on Drying techniques (LOD).

Reference hereinafter to a compound according to the invention includes compounds of the general formula (I) and their pharmaceutically acceptable salts, hydrates and solvates.

"Polymorphs": It will be appreciated by those skilled in the art that the compounds in accordance with the present invention can exist in several different crystalline forms due to a different arrangement of molecules in the crystal lattice. This may include solvate or hydrate (also known as pseudopolymorphs) and amorphous forms. All such crystalline forms and polymorphs are included within the scope of the invention. The polymorphs may be characterized by methods well known in the art. Examples of analytical procedures that may be used to determine whether polymorphism occurs include: melting point (including hot-stage microscopy), infrared (not in solution), X-ray powder diffraction, thermal analysis methods (e.g. differential scanning calorimetry (DSC), differential thermal analysis (DTA), thermogravimetric analysis (TGA)), Raman spectroscopy, comparative intrinsic dissolution rate, scanning electron microscopy (SEM).

In one aspect, the present invention provides novel compounds including:

Compound 1 (3S,4S)-3-[3-(4-Bromo-benzyl)-2,4-dioxo-1,3,8-triaza-spiro[4.5]dec-8-ylmethyl]-4-phenyl-pyrrolidine-1-carboxylic acid tert-butyl ester;

Compound 2 (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid tert-butyl ester;

Compound 3 (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 4 (3S,4S)-3-[1-Ethyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 5 (3S,4S)-3-[1-Isopropyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 6 (3S,4S)-3-[1-Isobutyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 7 (3S,4S)-3-(1-Ethyl-2,4-dioxo-3-propyl-1,3,8-triaza-spiro[4.5]dec-8-ylmethyl)-4-phenyl-pyrrolidine-1-carboxylic acid tert-butyl ester;

Compound 8 3-(4-Bromo-benzyl)-8-((3R,4S)-4-phenyl-pyrrolidin-3-ylmethyl)-1,3,8-triaza-spiro[4.5]decane-2,4-dione;

Compound 9 3-(4-Methoxy-benzyl)-8-((3R,4S)-4-phenyl-pyrrolidin-3-ylmethyl)-1,3,8-triaza-spiro[4.5]decane-2,4-dione;

Compound 10 3-(4-Methanesulfonyl-benzyl)-8-((3R,4S)-4-phenyl-pyrrolidin-3-ylmethyl)-1,3,8-triaza-spiro[4.5]decane-2,4-dione;

Compound 11 1-Ethyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 12 1-Isopropyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 13 1-Isobutyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 14 1-Ethyl-8-((3R,4S)-4-phenyl-pyrrolidin-3-ylmethyl)-3-propyl-1,3,8-triaza-spiro[4.5]decane-2,4-dione;

Compound 15 3-(4-Methanesulfonyl-benzyl)-8-((3S,4S)-4-phenyl-1-propionyl-pyrrolidin-3-ylmethyl)-1,3,8-triaza-spiro[4.5]decane-2,4-dione hydrochloride;

Compound 16 3-(4-Methanesulfonyl-benzyl)-8-[(3S,4S)-1-(1-methyl-cyclopropanecarbonyl)-4-phenyl-pyrrolidin-3-ylmethyl]-1,3,8-triaza-spiro[4.5]decane-2,4-dione hydrochloride;

Compound 17 8-[(3S,4S)-1-(2-Cyclopropyl-acetyl)-4-phenyl-pyrrolidin-3-ylmethyl]-3-(4-methanesulfonyl-benzyl)-1,3,8-triaza-spiro[4.5]decane-2,4-dione hydrochloride;

Compound 18 8-((3S,4S)-1-Cyclopentanecarbonyl-4-phenyl-pyrrolidin-3-ylmethyl)-3-(4-methanesulfonyl-benzyl)-1,3,8-triaza-spiro[4.5]decane-2,4-dione hydrochloride;

Compound 19 8-[(3S,4S)-1-(4,4-Difluoro-cyclohexanecarbonyl)-4-phenyl-pyrrolidin-3-ylmethyl]-3-(4-methanesulfonyl-benzyl)-1,3,8-triaza-spiro[4.5]decane-2,4-dione hydrochloride;

Compound 20 8-[(3S,4S)-1-(2-Fluoro-benzoyl)-4-phenyl-pyrrolidin-3-ylmethyl]-3-(4-methanesulfonyl-benzyl)-1,3,8-triaza-spiro[4.5]decane-2,4-dione hydrochloride;

Compound 21 8-[(3S,4S)-1-(2-Chloro-benzoyl)-4-phenyl-pyrrolidin-3-ylmethyl]-3-(4-methanesulfonyl-benzyl)-1,3,8-triaza-spiro[4.5]decane-2,4-dione hydrochloride;

Compound 22 4-{8-[(3S,4S)-1-(4,4-Difluoro-cyclohexanecarbonyl)-4-phenyl-pyrrolidin-3-ylmethyl]-2,4-dioxo-1,3,8-triaza-spiro[4.5]dec-3-ylmethyl}-N,N-dimethyl-benzenesulfonamide hydrochloride;

Compound 23 8-[(3S,4S)-1-(3,3-Dimethyl-butyryl)-4-phenyl-pyrrolidin-3-ylmethyl]-3-(4-methanesulfonyl-benzyl)-1,3,8-triaza-spiro[4.5]decane-2,4-dione hydrochloride;

Compound 24 8-[(3S,4S)-1-(3,3-Dimethyl-butyryl)-4-phenyl-pyrrolidin-3-ylmethyl]-1-ethyl-3-propyl-1,3,8-triaza-spiro[4.5]decane-2,4-dione hydrochloride;

Compound 25 8-[(3S,4S)-1-(3,3-Dimethyl-butyryl)-4-phenyl-pyrrolidin-3-ylmethyl]-1-ethyl-3-(4-methanesulfonyl-benzyl)-1,3,8-triaza-spiro[4.5]decane-2,4-dione hydrochloride;

Compound 26 1-Ethyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride;

Compound 27 8-((3S,4S)-1-Cyclopentanecarbonyl-4-phenyl-pyrrolidin-3-ylmethyl)-1-ethyl-3-(4-methanesulfonyl-benzyl)-1,3,8-triaza-spiro[4.5]decane-2,4-dione hydrochloride;

Compound 28 8-[(3S,4S)-1-(3,3-Dimethyl-butyryl)-4-phenyl-pyrrolidin-3-ylmethyl]-1-isopropyl-3-(4-methanesulfonyl-benzyl)-1,3,8-triaza-spiro[4.5]decane-2,4-dione hydrochloride;

Compound 29 1-Isopropyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride;

Compound 30 8-[(3S,4S)-1-(3,3-Dimethyl-butyryl)-4-phenyl-pyrrolidin-3-ylmethyl]-1-isobutyl-3-(4-methanesulfonyl-benzyl)-1,3,8-triaza-spiro[4.5]decane-2,4-dione hydrochloride;

Compound 31 1-Isobutyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride;

Compound 32 8-((3S,4S)-1-Cyclopentanecarbonyl-4-phenyl-pyrrolidin-3-ylmethyl)-1-isobutyl-3-(4-methanesulfonyl-benzyl)-1,3,8-triaza-spiro[4.5]decane-2,4-dione hydrochloride;

Compound 33 8-((3S,4S)-1-Cyclopropanecarbonyl-4-phenyl-pyrrolidin-3-ylmethyl)-3-(4-methoxy-benzyl)-1,3,8-triaza-spiro[4.5]decane-2,4-dione hydrochloride;

Compound 34 8-((3S,4S)-1-Cyclopropanecarbonyl-4-phenyl-pyrrolidin-3-ylmethyl)-3-(4-methanesulfonyl-benzyl)-1,3,8-triaza-spiro[4.5]decane-2,4-dione hydrochloride;

Compound 35 8-[(3S,4S)-1-(2-Cyclopropyl-acetyl)-4-phenyl-pyrrolidin-3-ylmethyl]-3-(4-methoxy-benzyl)-1,3,8-triaza-spiro[4.5]decane-2,4-dione hydrochloride;

Compound 36 8-[(3S,4S)-1-(3,3-Dimethyl-butyryl)-4-phenyl-pyrrolidin-3-ylmethyl]-1-ethyl-3-methyl-1,3,8-triaza-spiro[4.5]decane-2,4-dione hydrochloride;

Compound 37 8-[(3S,4S)-1-(3,3-Dimethyl-butyryl)-4-phenyl-pyrrolidin-3-ylmethyl]-1,3-diethyl-1,3,8-triaza-spiro[4.5]decane-2,4-dione hydrochloride;

Compound 38 3-Cyclopropylmethyl-8-[(3S,4S)-1-(3,3-dimethyl-butyryl)-4-phenyl-pyrrolidin-3-ylmethyl]-1-ethyl-1,3,8-triaza-spiro[4.5]decane-2,4-dione hydrochloride;

Compound 39 8-[(3S,4S)-1-(3,3-Dimethyl-butyryl)-4-phenyl-pyrrolidin-3-ylmethyl]-1-isopropyl-3-methyl-1,3,8-triaza-spiro[4.5]decane-2,4-dione hydrochloride;

Compound 40 8-[(3S,4S)-1-(3,3-Dimethyl-butyryl)-4-phenyl-pyrrolidin-3-ylmethyl]-1-isopropyl-3-ethyl-1,3,8-triaza-spiro[4.5]decane-2,4-dione hydrochloride;

Compound 41 3-Cyclopropylmethyl-8-[(3S,4S)-1-(3,3-dimethyl-butyryl)-4-phenyl-pyrrolidin-3-ylmethyl]-1-isopropyl-1,3,8-triaza-spiro[4.5]decane-2,4-dione hydrochloride;

Compound 42 8-[(3S,4S)-1-(3,3-Dimethyl-butyryl)-4-phenyl-pyrrolidin-3-ylmethyl]-1-isobutyl-3-methyl-1,3,8-triaza-spiro[4.5]decane-2,4-dione hydrochloride;

Compound 43 8-[(3S,4S)-1-(3,3-Dimethyl-butyryl)-4-phenyl-pyrrolidin-3-ylmethyl]-1-isobutyl-3-ethyl-1,3,8-triaza-spiro[4.5]decane-2,4-dione hydrochloride Compound 44 3-Cyclopropylmethyl-8-[(3S,4S)-1-(3,3-dimethyl-butyryl)-4-phenyl-pyrrolidin-3-ylmethyl]-1-isobutyl-1,3,8-triaza-spiro[4.5]decane-2,4-dione hydrochloride;

Compound 45 1-Cyclopropylmethyl-8-[(3S,4S)-1-(3,3-dimethyl-butyryl)-4-phenyl-pyrrolidin-3-ylmethyl]-3-methyl-1,3,8-triaza-spiro[4.5]decane-2,4-dione hydrochloride;

Compound 46 1-Cyclopropylmethyl-8-[(3S,4S)-1-(3,3-dimethyl-butyryl)-4-phenyl-pyrrolidin-3-ylmethyl]-3-ethyl-1,3,8-triaza-spiro[4.5]decane-2,4-dione hydrochloride;

Compound 47 1,3-Bis-cyclopropylmethyl-8-[(3S,4S)-1-(3,3-dimethyl-butyryl)-4-phenyl-pyrrolidin-3-ylmethyl]-1,3,8-triaza-spiro[4.5]decane-2,4-dione hydrochloride;

Compound 48 (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid dimethylamide hydrochloride;

Compound 49 (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid dimethylamide hydrochloride;

Compound 50 8-((3S,4S)-1-Benzenesulfonyl-4-phenyl-pyrrolidin-3-ylmethyl)-3-(4-methoxy-benzyl)-1,3,8-triaza-spiro[4.5]decane-2,4-dione hydrochloride;

Compound 51 8-((3S,4S)-1-Benzenesulfonyl-4-phenyl-pyrrolidin-3-ylmethyl)-3-(4-methanesulfonyl-benzyl)-1,3,8-triaza-spiro[4.5]decane-2,4-dione hydrochloride;

Compound 52 8-((3S,4S)-1-Cyclohexylmethyl-4-phenyl-pyrrolidin-3-ylmethyl)-3-(4-methoxy-benzyl)-1,3,8-triaza-spiro[4.5]decane-2,4-dione dihydrochloride;

Compound 53 8-((3S,4S)-1-Cyclohexylmethyl-4-phenyl-pyrrolidin-3-ylmethyl)-3-(4-methanesulfonyl-benzyl)-1,3,8-triaza-spiro[4.5]decane-2,4-dione dihydrochloride;

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.1 to about 750 mg/kg of body weight per day, preferably in the range of 0.5 to 60 mg/kg/day, most preferably in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, preferably about 2 to 50 µM, most preferably about 3 to about 30 µM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation. The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulation suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

When the compound (I) or a pharmaceutically acceptable salt, hydrate or solvate thereof is used in combination with a second therapeutic active agent, the dose of each compound may be either the same as or different from that when the compound is used alone. Conventional doses and regimens are readily appreciated by those skilled in the art, including doses described in the Physicians Desk Reference, 56$^{th}$ edition, 2002.

The present invention is directed to the use of the compounds as modulators of CCR5 chemokine receptor activity. In particular, the compounds of the invention may be tested for binding to the CCR5 receptor in the Chemokine Binding assay, as described. The terms "modulator" or "modulation" are meant to include antagonism, agonism, mixed and partial antagonism and agonism.

Compounds of the present invention can also be tested for anti-HIV activity in an assay as described in the HIV-1 Replication in PBMC Cultures assay or in the HIV-1 Replication in PM1 cells.

The following general schemes and examples are provided to illustrate various embodiments of the present invention and shall not be considered as limiting in scope.

The following abbreviations may be used as follows:
br broad
DCE 1,2-dichloroethane
DCM dichloromethane
DMF N,N-dimethylformamide
Hal halogen
TFA trifluoroacetic acid The semi-preparative HPLC purification procedure that can be used is described below:
Column: Phenomenex Luna $C_{18}$ (2), 5 microns, 10×250 mm
Buffer A: 3 mM HCl in $H_2O$ (pH 2.4-2.6)
Buffer B: acetonitrile
Method A: 15 to 45% B in 30 min. (15 mL/min)

EXAMPLE 1

Preparation of
(3R,4S)-3-formyl-4-phenyl-pyrrolidine-1-carboxylic acid tert-butyl ester

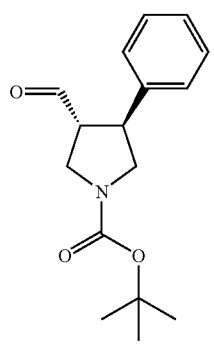

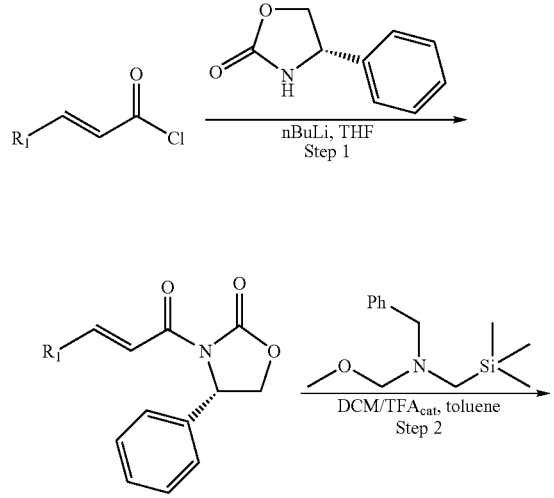

Scheme 1

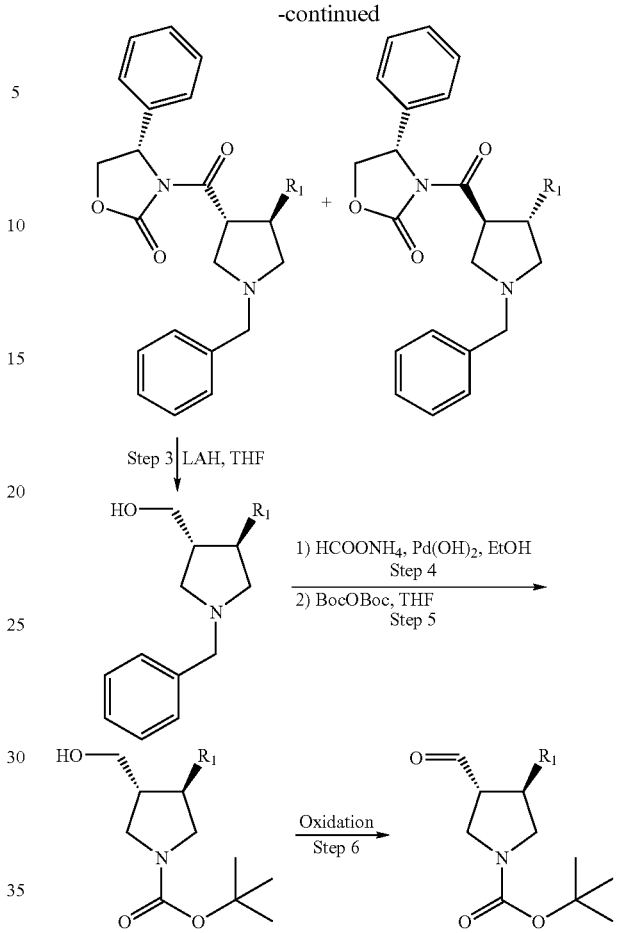

Step 1: To (S)-(+)-4-phenyl-2-oxazolidinone (9.88 g, 60 mmol) in THF (150 mL) at −78° C., was added n-butyl lithium (37.7 mL, 1.6M in hexanes, 60 mmol) over a period of 30 minutes. THF (50 mL) was added to the resultant thick suspension and the reaction mixture allowed to warm up to facilitate stirring. Trans-cinnamoylchloride (11.5 g, 69 mmol) in THF (30 mL) was added dropwise. The reaction was stirred at room temperature overnight. The reaction mixture was quenched with a saturated ammonium chloride solution (50 mL) and stirred for 0.5 h. The solvent was removed in vacuo, the residue dissolved in ethyl acetate, washed with water (300 mL), 5% sodium bicarbonate (200 mL) and brine (100 mL) and dried over sodium sulfate. The solvent was removed in vacuo to give a pale yellow solid. The compound was crystallized from ethylacetate and washed with hexanes to give 17.12 g (97%) of (S)-4-phenyl-3-[(E)-(3-phenyl-acryloyl)]-oxazolidin-2-one.

$^1$H NMR (400 MHz, $CDCl_3$): δ [ppm] 7.92 (d, 1H), 7.77 (d, 1H), 7.59 (m, 2H), 7.40-7.35 (m, 8H), 5.55 (dd, 1H), 4.74 (t, 1H), 4.31 (dd, 1H).

Step 2: N-Benzyl-N-(methoxymethyl)trimethylsilylmethylamine (10.03 g, 40.5 mmol) was added to (S)-4-phenyl-3-[(E)-(3-phenyl-acryloyl)]-oxazolidin-2-one (10.3 g, 35.1 mmol) in toluene (150 mL) at 0° C. and the mixture was stirred for 20 minutes. Trifluoroacetic acid (9.7 mL) in dichloromethane (125 mL) was added dropwise to the reaction mixture keeping the internal temperature at 0° C. The reaction was stirred at room temperature overnight.

The reaction mixture was poured into saturated sodium bicarbonate (200 mL) and extracted with dichloromethane (2×75 mL). The combined organic phases were washed with brine and dried over sodium sulfate. The organic phases were concentrated to give a waxy solid, which was purified by flash silica gel chromatography eluting with ethyl acetate: hexanes (1:9) to give 9.68 g (61%) of (S)-3-((3R,4S)-1-benzyl-4-phenyl-pyrrolidine-3-carbonyl)-4-phenyl-oxazolidin-2-one.

$^1$H NMR (400 MHz, CDCl$_3$): δ [ppm] 7.33-7.11 (m, 15H), 5.31 (m, 1H), 4.53 (t, 1H), 4.11 (m, 2H), 3.93 (q, 1H), 3.67 (dd, 1H), 3.48 (d, 1H), 3.22 (t, 1H), 3.03 (t, 1H), 2.69 (dd, 1H), 2.60 (t, 1H).

Step 3: To (S)-3-((3R,4S)-1-benzyl-4-phenyl-pyrrolidine-3-carbonyl)-4-phenyl-oxazolidin-2-one (9.96 g, 23.35 mmol) in THF (100 mL) in a three-necked flask equipped with a thermometer and addition funnel was added lithium aluminium hydride (48 mL, 1M in THF) dropwise so that the temperature did not exceed 40° C. When addition was complete, the reaction was stirred at room temperature overnight. The reaction was carefully quenched with water (1.6 mL), NaOH (1.6 mL, 2N) and water (4.5 mL). After stirring for 15 minutes, the reaction mixture was filtered through a pad of celite and rinsed with THF (40 mL). The filtrate was concentrated to give a pale yellow oil, which was purified by flash silica gel chromatography eluting with ethyl acetate: hexanes (1:1) to give 3.38 g (55%) of ((3R,4S)-1-benzyl-4-phenyl-pyrrolidin-3-yl)-methanol.

$^1$H NMR (400 MHz, CDCl$_3$): δ [ppm] 7.4-7.2 (m, 10H), 3.73 (m, 2H), 3.66 (m, 2H), 3.3-3.2 (m, 2H), 2.9-2.8 (m, 2H), 2.5-2.4 (m,2H). LC/MS: m/z 267 (MH$^+$).

Step 4: To ((3R,4S)-1-benzyl-4-phenyl-pyrrolidin-3-yl)-methanol (2.28 g, 8.54 mmol) in ethanol (200 mL) was added ammonium formate (5.39 g, 85.49 mmol) and palladium hydroxide (446 mg, 20 wt % Pd) and the mixture was refluxed for 1.5 h. Ammonia in methanol (0.8 mL, 2M) was added to the reaction mixture and refluxed for an additional 0.5 h. The reaction mixture was filtered through celite and concentrated to give ((3R,4S)-4-phenyl-pyrrolidin-3-yl)-methanol as a colorless oil (1.25 g) which was used directly in the next step.

Step 5: To ((3R,4S)-4-phenyl-pyrrolidin-3-yl)-methanol (1.25 g, 7.05 mmol) in THF (35 mL) was added triethylamine (0.97 mL, 7.05 mmol) at room temperature. The reaction mixture was cooled to 0° C. and di-tert-butyl dicarbonate (1.53 g, 7.05 mmol) dissolved in THF (10 mL) was added. The reaction mixture was stirred overnight at room temperature. Then the reaction mixture was concentrated to give a colorless oil, which was purified by flash silica gel chromatography eluting with ethyl acetate: hexanes (2:3) to give 1.31 g (70%) of (3R,4S)-3-hydroxymethyl-4-phenyl-pyrrolidine-1-carboxylic acid tert-butyl ester.

$^1$H NMR (400 MHz, CDCl$_3$): δ [ppm] 7.31 (m, 2H), 7.23 (m, 3H), 3.82 (m, 1H), 3.76 (m, 1H), 3.66 (dd, 1H), 3.52 (dd, 1H), 3.38 (t, 1H), 3.28 (t, 1H), 3.11 (m, 2H), 2.49 (m, 2H), 1.46 (s, 9H).

Step 6: Oxalyl chloride (3.3 mL, 2M in CH$_2$Cl$_2$, 6.42 mmol) was stirred in dichloromethane (3 mL) in a three-necked flask. The reaction mixture was cooled to −78° C., and dimethyl sulfoxide (0.91 mL, 12.85 mmol) was added so that the internal temperature did not exceed −65° C. The reaction mixture was then stirred for 15 minutes. The (3R,4S)-3-hydroxymethyl-4-phenyl-pyrrolidine-1-carboxylic acid tert-butyl ester (713 mg, 2.57 mmol) in dichloromethane (6 mL) was added dropwise keeping the internal temperature below −65° C. and then stirred for 15 minutes. Diisopropylethylamine (4.5 mL, 25.7 mmol) was added keeping the internal temperature below −65° C. and then stirred for 20 minutes. The cooling bath was removed and the reaction mixture was stirred at room temperature for 2 h. The reaction mixture was concentrated to give a colorless oil, which was purified by flash silica gel chromatography eluting with ethyl acetate: hexanes (1:4) to give 496 mg (70%) of (3R,4S)-3-formyl-4-phenyl-pyrrolidine-1-carboxylic acid tert-butyl ester.

$^1$H NMR (400 MHz, CDCl$_3$): δ [ppm] 9.65 (s, 1H), 7.36-7.32 (m, 5H), 4.0-3.4 (m, 6H), 3.20 (m, 1H), 1.46 (s,9H).

EXAMPLE 2

General Procedure for the Production of Compounds of Scheme 2

N3 alkylation of 2,4-dioxo-1,3,8-triaza-spiro[4.5]decane-8-carboxylic acid tert-butyl ester takes place in solvents such as DMF or DMA at room temperature using an inorganic base such as Na$_2$CO$_3$, K$_2$CO$_3$ or Cs$_2$CO$_3$. (see P. W. Smith et al. *J. Med. Chem.* 1995, 38, 3772-3779) with halogenoalkyl derivative. The intermediate 1-1 can then be optionally N1 substituted by alkylation (see K. H. Bleicher et al. *Bioorg. Med. Chem. Lett.* 2002, 12, 2519-2522) or arylation, giving access to intermediate 1-2, and deprotected under acidic conditions such as acid hydrochloride in dioxane. The chlorohydrate 1-3 is condensed to chiral aldehyde 1-4 using conventional reductive amination reaction condition (see Abdel-Magid A. F. et al. *J. Org. Chem.* 1996, 61, 3849-3862). Further deprotection of chiral pyrrolidine 1-5 under acidic condition such a mixture of TFA in DCM provides the pyrrolidine 1-6.

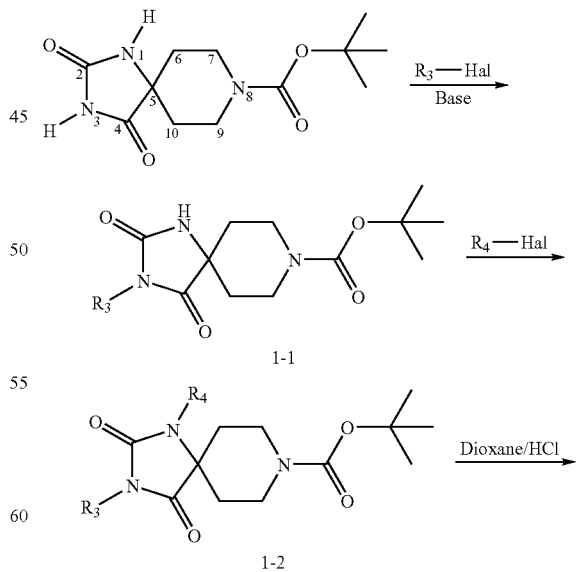

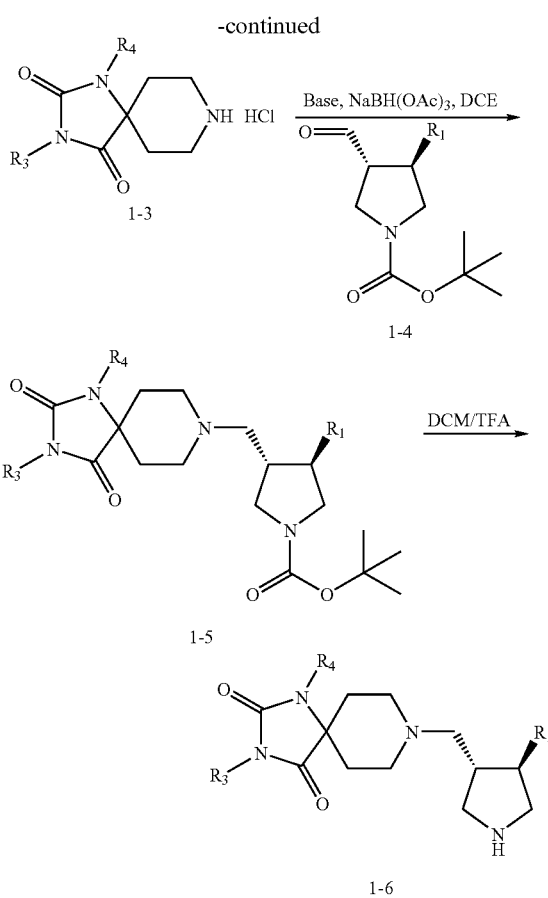

EXAMPLE 2A 3-(4-Methoxybenzyl)-2,4-dioxo-1,3,8-triazaspiro[4.5]decane-8-carboxylic acid tert-butyl ester

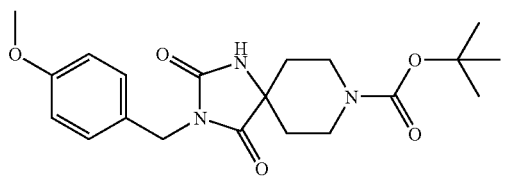

To 1 g (3.7 mmol) of 2,4-dioxo-1,3,8-triaza-spiro[4.5]decane-8-carboxylic acid tert-butyl ester were added successively 554 μL (4.08 mmol) of 4-methoxybenzyl chloride, 565 mg (4.08 mmol) of potassium carbonate and 37 mL of anhydrous DMF. The reaction mixture was stirred overnight at room temperature. Then 250 mL of water were added and a white precipitated solid was collected by filtration. This crude material was back washed with diethyl ether and dried under reduced pressure yielding 1.15 g (79%) of 3-(4-methoxybenzyl)-2,4-dioxo-1,3,8-triazaspiro[4.5]decane-8-carboxylic acid tert-butyl ester as a white solid.

$^1$H NMR (400 MHz, CD$_2$Cl$_2$): δ [ppm] 7.27 (d, 2H), 6.85 (d, 2H) 6.16 (s, 1H), 4.57 (s, 2H), 3.96 (m, 2H), 3.78 (s, 3H), 3.17 (m, 2H), 1.95 (m, 2H), 1.58 (m, 2H), 1.45 (s, 9H).

EXAMPLE 2B 3-(4-Methoxybenzyl)-1,3,8-triaza-spiro[4.5]decane-2,4-dione hydrochloride

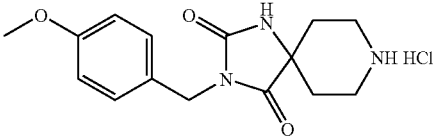

To 1.15 g (2.95 mmol) of 3-(4-methoxybenzyl)-2,4-dioxo-1,3,8-triazaspiro[4.5]decane-8-carboxylic acid tert-butyl ester was added 8 mL of dioxane and 6 mL of 4N solution of dioxane/HCl. The reaction mixture was stirred for 2 hours at room temperature and concentrated in vacuo. The crude was dissolved in a minimum of methanol and diethyl ether was added to obtain, after filtration, 3-(4-methoxybenzyl)-1,3,8-triaza-spiro[4.5]decane-2,4-dione hydrochloride as a white solid (644 mg, 67%).

$^1$H NMR (400 MHz, DMSO-d$_6$): δ [ppm] 9.22 (br s, 1H), 9.05 (s, 1H), 8.89 (br s, 1H), 7.16 (d, 2H), 6.87 (d, 2H), 4.44 (s, 2H), 3.71 (s, 3H), 3.29 (m, 2H), 3.13 (m, 2H), 2.06 (m, 2H) 1.77 (br d, 2H).

EXAMPLE 2C 3-(4-Methoxy-benzyl)-1-methyl-2,4-dioxo-1,3,8-triaza-spiro[4.5]decane-8-carboxylic acid tert-butyl ester

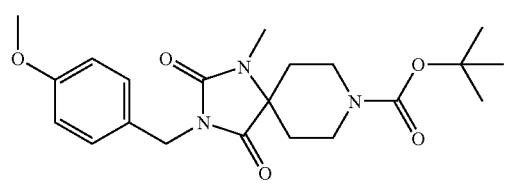

390 mg (1 mmol) of 3-(4-methoxybenzyl)-2,4-dioxo-1,3,8-triazaspiro[4.5]decane-8-carboxylic acid tert-butyl ester were solubilized in 5 mL of DMF under nitrogen before adding 61 mg (1.5 mmol) of sodium hydride in mineral oil 60%. The reaction mixture was agitated for 5 minutes before the addition of 70 μL (1.1 mmol) of iodomethane. After 2 hours of agitation at room temperature, the reaction mixture was quenched with 20 mL of water and then extracted with diethyl ether (2×20 mL). The organic layers were dried over sodium sulfate, filtrated and evaporated in vacuo to give quantitatively 3-(4-methoxy-benzyl)-1-methyl-2,4-dioxo-1,3,8-triaza-spiro[4.5]decane-8-carboxylic acid tert-butyl ester (404 mg) as a yellowish oil.

$^1$H NMR (400 MHz, DMSO-d$_6$): δ [ppm] 7.14 (d, 2H), 6.85 (d, 2H), 4.44 (s, 2H), 3.91 (br s, 2H), 3.69 (s, 3H), 3.27 (br s, 2H), 2.73 (s, 3H), 1.82 (m, 2H), 1.58 (d, 2H), 1.38 (s, 9H).

EXAMPLE 2D

3-(4-Methoxy-benzyl)-1-methyl-1,3,8-triaza-spiro[4.5]decane-2,4-dione hydrochloride

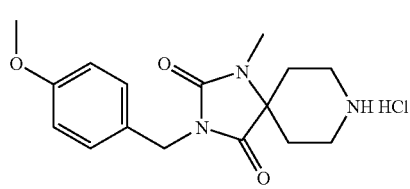

403 mg (1 mmol) of 3-(4-methoxy-benzyl)-1-methyl-2,4-dioxo-1,3,8-triaza-spiro[4.5]decane-8-carboxylic acid tert-butyl ester were dissolved in a minimum of diethyl ether before adding 3 mL of a solution of dioxane/HCl 4N. The reaction mixture was agitated 10 minutes at room temperature and then evaporated. The yellow crude was triturated with diethyl ether and filtered to yield 115.3 mg (34%) of 3-(4-methoxy-benzyl)-1-methyl-1,3,8-triaza-spiro[4.5]decane-2,4-dione hydrochloride as a pale yellow solid.

$^1$H NMR (400 MHz, DMSO-$d_6$): δ [ppm] 9.14 (br s, 2H), 7.15 (d, 2H), 6.85 (d, 2H), 4.45 (s, 2H), 3.69 (s, 3H), 3.30 (br s, 4H), 2.74 (s, 3H), 2.30 (m, 2H), 1.80 (d, 2H).

EXAMPLE 3

(3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid tert-butyl ester (Compound 3)

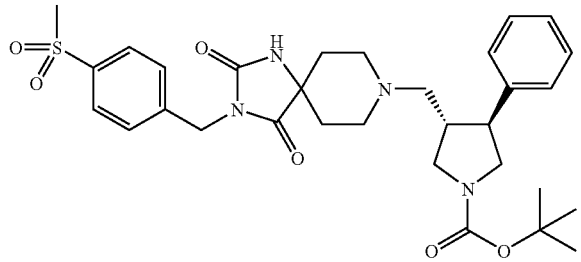

To 187 mg (0.50 mmol) of 3-(4-methanesulfonyl-benzyl)-1,3,8-triaza-spiro[4.5]decane-2,4-dione hydrochloride was added 5 mL of DCM followed by 0.066 mL of triethylamine (0.50 mmol) and a solution of (3R,4S)-3-formyl-4-phenyl-pyrrolidine-1-carboxylic acid tert-butyl ester (0.93 mL of a 148 mg/mL solution, 0.50 mmol). The solution was stirred at room temperature for 30 minutes and sodium triacetoxyborohydride was added (159 mg, 0.75 mmol). The solution was stirred overnight. The resulting mixture was evaporated to dryness and purified by chromatography on Bond Elute™ (10 g) using 1:1 EtOAc:Hexane followed by 1% methanol in DCM. After evaporation of the desired fractions, 93 mg (31%) of (3S,4S)-3-[3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester as a white solid were obtained.

EXAMPLE 4

3-(4-Methanesulfonyl-benzyl)-8-((3R,4S)-4-phenyl-pyrrolidin-3-ylmethyl)-1,3,8-triaza-spiro[4.5]decane-2,4-dione (Compound 10)

83 mg (0.139 mmol) of (3S,4S)-3-[3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester was dissolved in 3 mL of DCM and 1 mL of TFA and the solution was stirred overnight. The mixture was then evaporated to dryness and the residue was redissolved in 2 mL of toluene and evaporated again at 40° C. The crude compound was then dissolved in 5 mL of 5% methanol in DCM and filtered through a ChemElute™ loaded with 1 mL of 2 M NaOH. The filtrate was evaporated to yield 3-(4-methanesulfonyl-benzyl)-8-((3R,4S)-4-phenyl-pyrrolidin-3-ylmethyl)-1,3,8-triaza-spiro[4.5]decane-2,4-dione (52.1 mg, 76%).

EXAMPLE 5

General Procedure for the Synthesis of Compounds of Scheme 3

Scheme 3

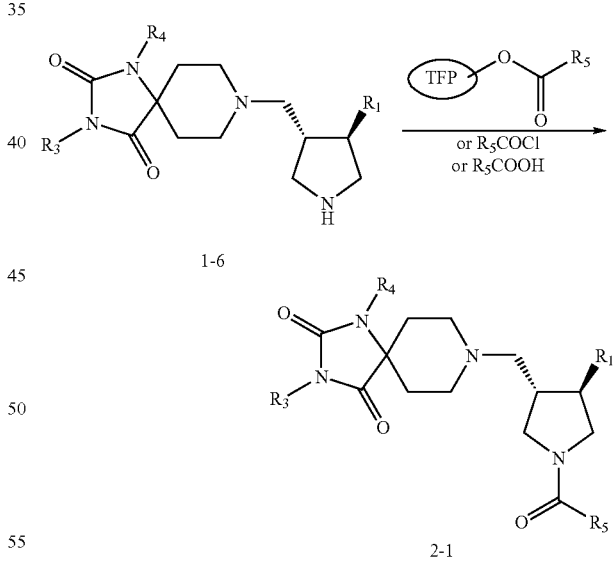

The pyrrolidine 1-6 is condensed with preactivated carboxylic acid $R_5$COOH on polymeric 4-hydroxy-2,3,5,6-tetrafluorobenzamido (TFP) resin (see preparation in J. M. Salvino et al. *J. Comb. Chem.* 2000, 2, 691-697) in solvent such as DMF, or condensed with acid chloride $R_5$COCl in solvent such as DCM in presence of a base such as triethylamine or diisopropylethylamine, or condensed with a carboxylic acid $R_5$COOH in solvent such as DMF with coupling agents such as HOBt, DIC, HATU, BOP, PyBOP, to provide acylated compound 2-1.

EXAMPLE 5A

8-[(3S,4S)-1-(3,3-Dimethyl-butyryl)-4-phenyl-pyrrolidin-3-ylmethyl]-3-(4-methanesulfonyl-benzyl)-1,3,8-triaza-spiro[4.5]decane-2,4-dione hydrochloride (Compound 23)

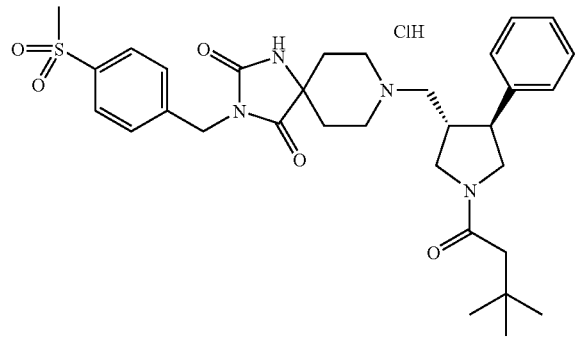

25.5 mg (0.051 mmol) of 3-(4-methanesulfonyl-benzyl)-8-((3R,4S)-4-phenyl-pyrrolidin-3-ylmethyl)-1,3,8-triaza-spiro[4.5]decane-2,4-dione dissolved in 1 mL of anhydrous DMF was added to 100 mg (0.134 mmol, loading of 1.34 mmol/g) of 3,3-dimethylbutanecarboxyl activated ester on polymeric 4-hydroxy-2,3,5,6-tetrafluorobenzamido (TFP) resin (see preparation in J. M. Salvino et al. *J. Comb. Chem.* 2000, 2, 691-697) preswollen in 0.5 mL of DMF. After overnight agitation, the suspension was filtered and the resin was washed with DCM. The filtrate was evaporated and the residue was purified by semi-preparative HPLC (Method A). After lyophilization of the desired fractions, 6.7 mg (21%) of 8-[(3S,4S)-1-(3,3-dimethyl-butyryl)-4-phenyl-pyrrolidin-3-ylmethyl]-3-(4-methanesulfonyl-benzyl)-1,3,8-triaza-spiro[4.5]decane-2,4-dione hydrochloride as a white solid were obtained.

Table 1 of compounds illustrates some of the compounds of the present invention which were synthesized using the procedures generally described in examples 1 to 5 and generally described in schemes 1, 2 and 3.

TABLE 1

| CPD# | STRUCTURE | IC$_{50}$ HIV-1 PM1 | COMPOUND NAME |
|---|---|---|---|
| 1 | 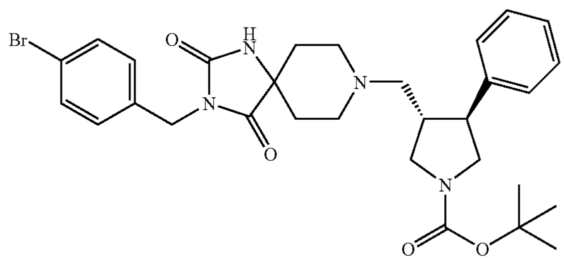 | <1 μM | (3S,4S)-3-[3-(4-Bromo-benzyl)-2,4-dioxo-1,3,8-triaza-spiro[4.5]dec-8-ylmethyl]-4-phenyl-pyrrolidine-1-carboxylic acid tert-butyl ester |
| 2 | 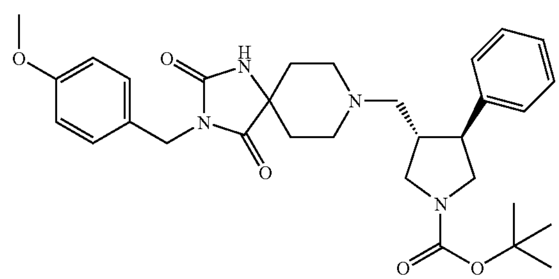 | <1 μM | (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid tert-butyl ester |
| 3 | 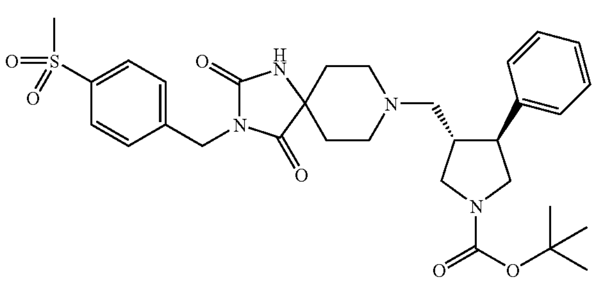 | <1 μM | (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid tert-butyl ester |

TABLE 1-continued

| CPD# | STRUCTURE | IC$_{50}$ HIV-1 PM1 | COMPOUND NAME |
|---|---|---|---|
| 4 | 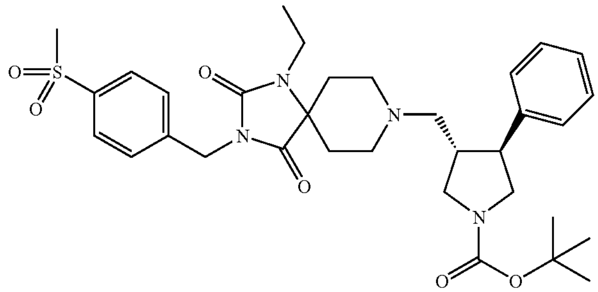 | | (3S,4S)-3-[1-Ethyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester |
| 5 | 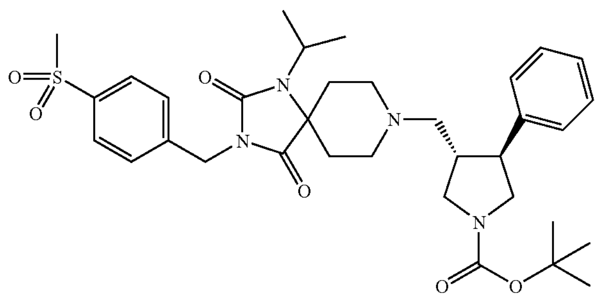 | | (3S,4S)-3-[1-Isopropyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester |
| 6 | 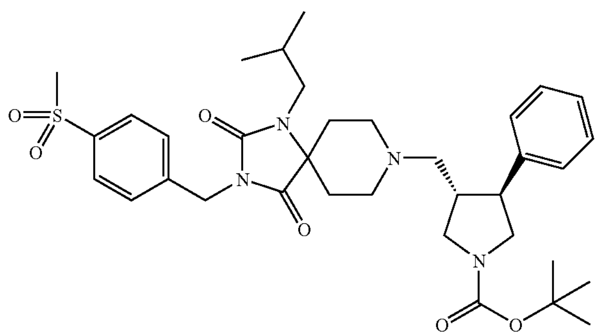 | | (3S,4S)-3-[1-Isobutyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester |
| 7 | 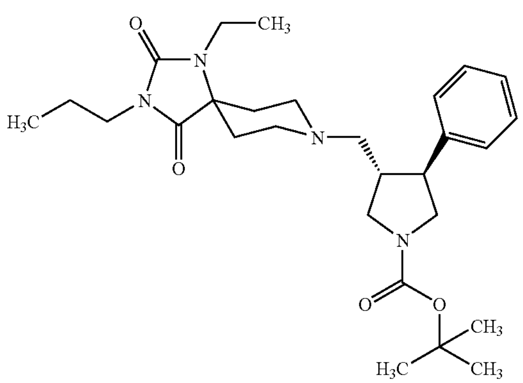 | | (3S,4S)-3-(1-Ethyl-2,4-dioxo-3-propyl-1,3,8-triaza-spiro[4.5]dec-8-ylmethyl)-4-phenyl-pyrrolidine-1-carboxylic acid tert-butyl ester |
| 8 | 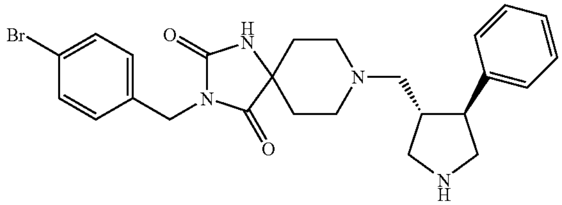 | | 3-(4-Bromo-benzyl)-8-((3R,4S)-4-phenyl-pyrrolidin-3-ylmethyl)-1,3,8-triaza-spiro[4.5]decane-2,4-dione |

TABLE 1-continued

| CPD# | STRUCTURE | IC₅₀ HIV-1 PM1 | COMPOUND NAME |
|---|---|---|---|
| 9 | 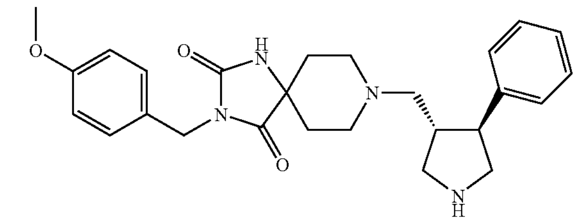 | | 3-(4-Methoxy-benzyl)-8-((3R,4S)-4-phenyl-pyrrolidin-3-ylmethyl)-1,3,8-triaza-spiro[4.5]decane-2,4-dione |
| 10 | 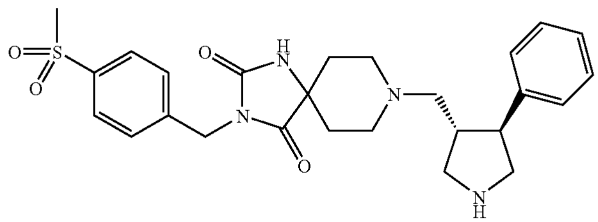 | | 3-(4-Methanesulfonyl-benzyl)-8-((3R,4S)-4-phenyl-pyrrolidin-3-ylmethyl)-1,3,8-triaza-spiro[4.5]decane-2,4-dione |
| 11 | 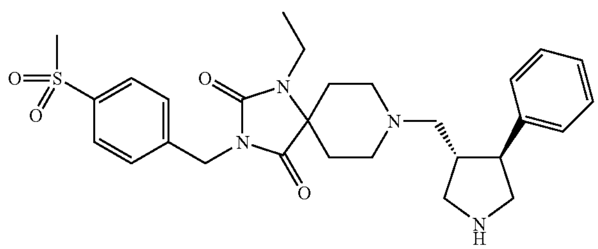 | | 1-Ethyl-3-(4-methanesulfonyl-benzyl)-8-((3R,4S)-4-phenyl-pyrrolidin-3-ylmethyl)-1,3,8-triaza-spiro[4.5]decane-2,4-dione |
| 12 | 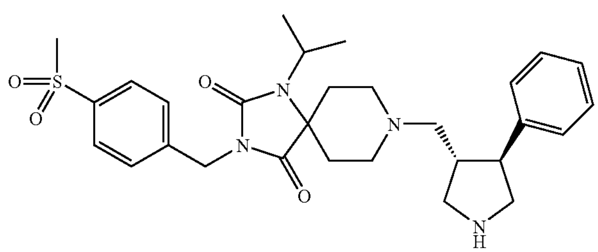 | | 1-Isopropyl-3-(4-methanesulfonyl-benzyl)-8-((3R,4S)-4-phenyl-pyrrolidin-3-ylmethyl)-1,3,8-triaza-spiro[4.5]decane-2,4-dione |
| 13 | 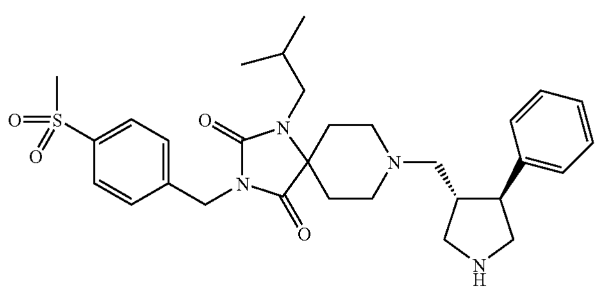 | | 1-Isobutyl-3-(4-methanesulfonyl-benzyl)-8-((3R,4S)-4-phenyl-pyrrolidin-3-ylmethyl)-1,3,8-triaza-spiro[4.5]decane-2,4-dione |
| 14 | 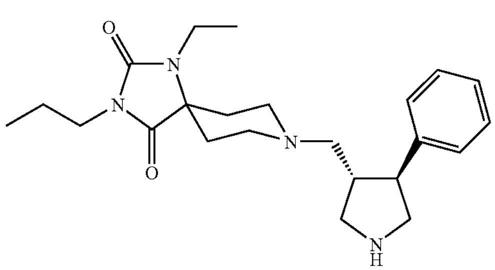 | | 1-Ethyl-8-((3R,4S)-4-phenyl-pyrrolidin-3-ylmethyl)-3-propyl-1,3,8-triaza-spiro[4.5]decane-2,4-dione |

TABLE 1-continued

| CPD# | STRUCTURE | IC$_{50}$ HIV-1 PM1 | COMPOUND NAME |
|---|---|---|---|
| 15 | 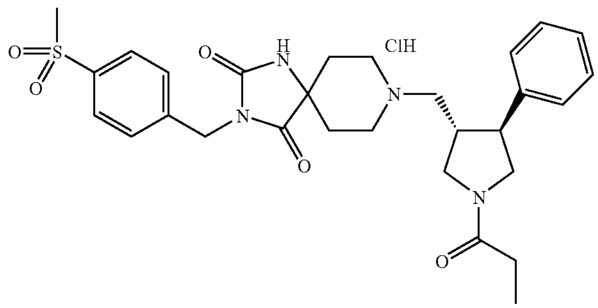 | <1 μM | 3-(4-Methanesulfonyl-benzyl)-8-((3S,4S)-4-phenyl-1-propionyl-pyrrolidin-3-ylmethyl)-1,3,8-triaza-spiro[4.5]decane-2,4-dione hydrochloride |
| 16 | 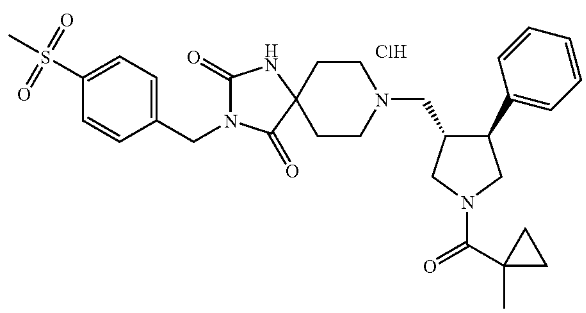 | <1 μM | 3-(4-Methanesulfonyl-benzyl)-8-[(3S,4S)-1-(1-methyl-cyclopropanecarbonyl)-4-phenyl-pyrrolidin-3-ylmethyl]-1,3,8-triaza-spiro[4.5]decane-2,4-dione hydrochloride |
| 17 | 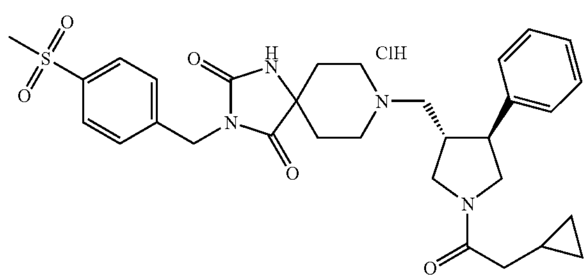 | <1 μM | 8-[(3S,4S)-1-(2-Cyclopropyl-acetyl)-4-phenyl-pyrrolidin-3-ylmethyl]-3-(4-methanesulfonyl-benzyl)-1,3,8-triaza-spiro[4.5]decane-2,4-dione hydrochloride |
| 18 | 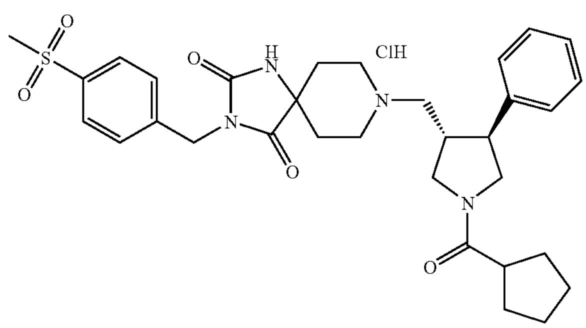 | <1 μM | 8-((3S,4S)-1-Cyclopentanecarbonyl-4-phenyl-pyrrolidin-3-ylmethyl)-3-(4-methanesulfonyl-benzyl)-1,3,8-triaza-spiro[4.5]decane-2,4-dione hydrochloride |

TABLE 1-continued

| CPD# | STRUCTURE | IC$_{50}$ HIV-1 PM1 | COMPOUND NAME |
|---|---|---|---|
| 19 | 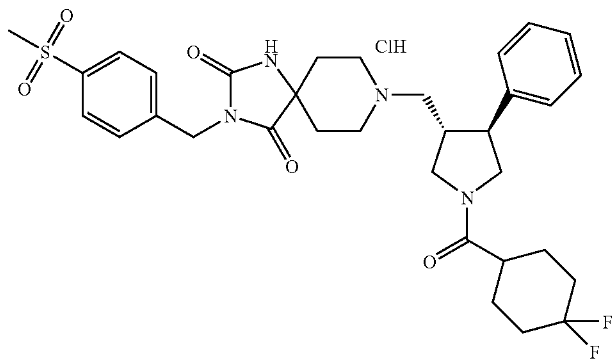 | <1 μM | 8-[(3S,4S)-1-(4,4-Difluoro-cyclohexanecarbonyl)-4-phenyl-pyrrolidin-3-ylmethyl]-3-(4-methanesulfonyl-benzyl)-1,3,8-triaza-spiro[4.5]decane-2,4-dione hydrochloride |
| 20 | 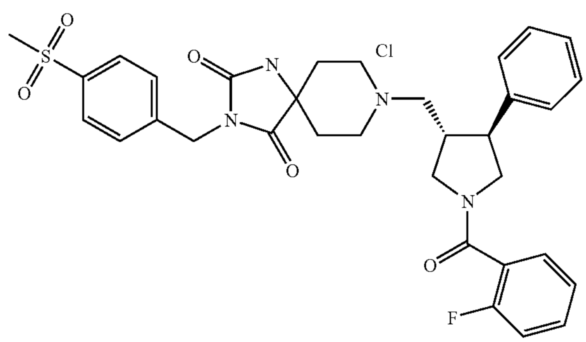 | <1 μM | 8-[(3S,4S)-1-(2-Fluoro-benzoyl)-4-phenyl-pyrrolidin-3-ylmethyl]-3-(4-methanesulfonyl-benzyl)-1,3,8-triaza-spiro[4.5]decane-2,4-dione hydrochloride |
| 21 | 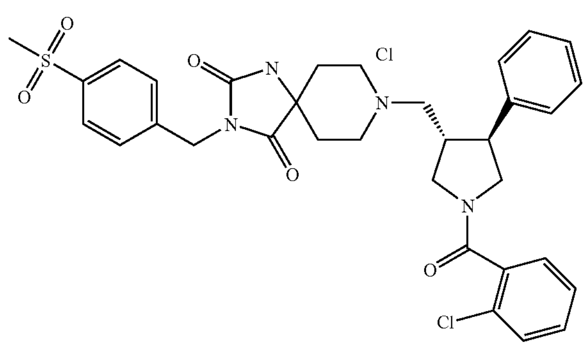 | <1 μM | 8-[(3S,4S)-1-(2-Chloro-benzoyl)-4-phenyl-pyrrolidin-3-ylmethyl]-3-(4-methanesulfonyl-benzyl)-1,3,8-triaza-spiro[4.5]decane-2,4-dione hydrochloride |
| 22 | 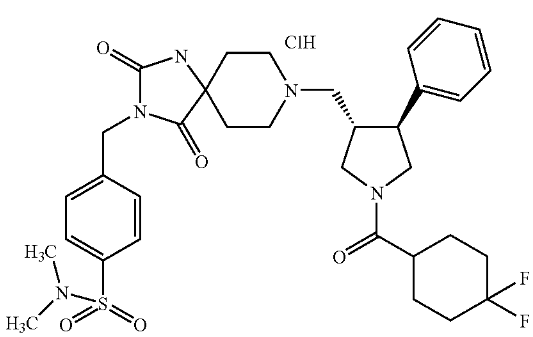 | <1 μM | 4-{8-[(3S,4S)-1-(4,4-Difluoro-cyclohexanecarbonyl)-4-phenyl-pyrrolidin-3-ylmethyl]-2,4-dioxo-1,3,8-triaza-spiro[4.5]dec-3-ylmethyl}-N,N-dimethyl-benzenesulfonamide hydrochloride |

TABLE 1-continued

| CPD# | STRUCTURE | IC$_{50}$ HIV-1 PM1 | COMPOUND NAME |
|---|---|---|---|
| 23 | 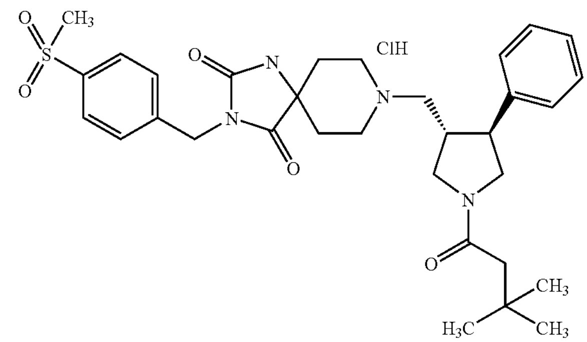 | <1 μM | 8-[(3S,4S)-1-(3,3-Dimethyl-butyryl)-4-phenyl-pyrrolidin-3-ylmethyl]-3-(4-methanesulfonyl-benzyl)-1,3,8-triaza-spiro[4.5]decane-2,4-dione hydrochloride |
| 24 | 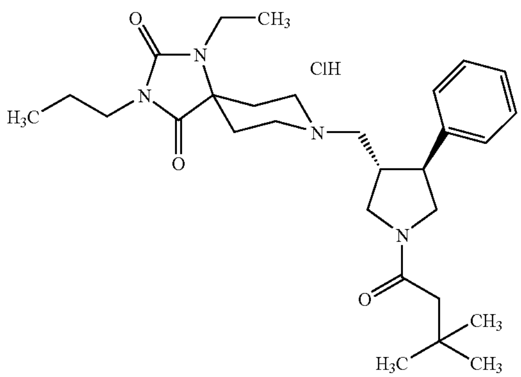 | | 8-[(3S,4S)-1-(3,3-Dimethyl-butyryl)-4-phenyl-pyrrolidin-3-ylmethyl]-1-ethyl-3-propyl-1,3,8-triaza-spiro[4.5]decane-2,4-dione hydrochloride |
| 25 | 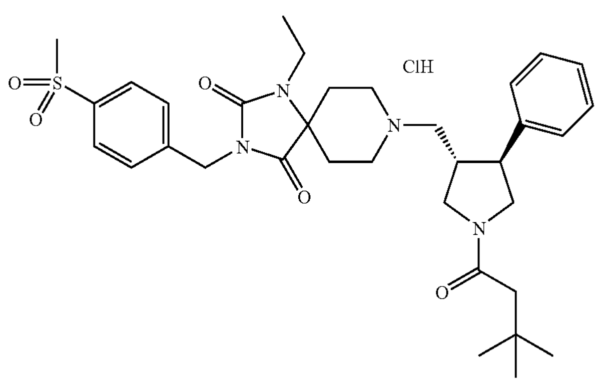 | | 8-[(3S,4S)-1-(3,3-Dimethyl-butyryl)-4-phenyl-pyrrolidin-3-ylmethyl]-1-ethyl-3-(4-methanesulfonyl-benzyl)-1,3,8-triaza-spiro[4.5]decane-2,4-dione hydrochloride |
| 26 | 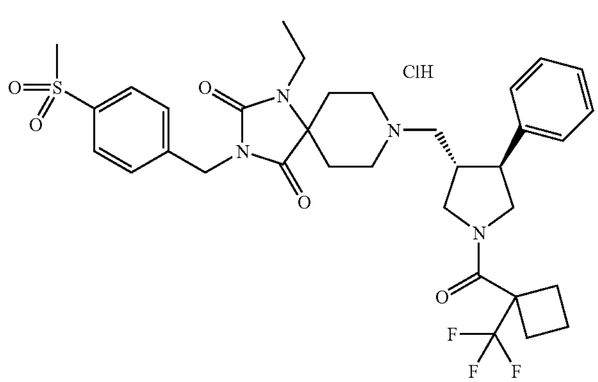 | | 1-Ethyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride |

TABLE 1-continued

| CPD# | STRUCTURE | IC$_{50}$ HIV-1 PM1 | COMPOUND NAME |
| --- | --- | --- | --- |
| 27 | 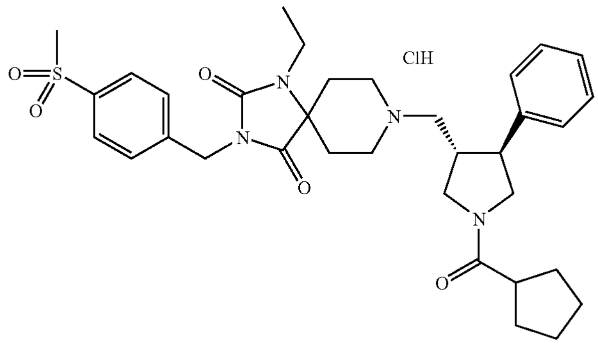 | | 8-((3S,4S)-1-Cyclopentanecarbonyl-4-phenyl-pyrrolidin-3-ylmethyl)-1-ethyl-3-(4-methanesulfonyl-benzyl)-1,3,8-triaza-spiro[4.5]decane-2,4-dione hydrochloride |
| 28 | 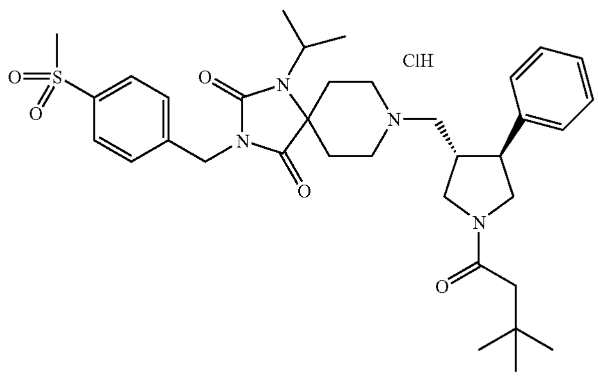 | | 8-[(3S,4S)-1-(3,3-Dimethyl-butyryl)-4-phenyl-pyrrolidin-3-ylmethyl]-1-isopropyl-3-(4-methanesulfonyl-benzyl)-1,3,8-triaza-spiro[4.5]decane-2,4-dione hydrochloride |
| 29 | 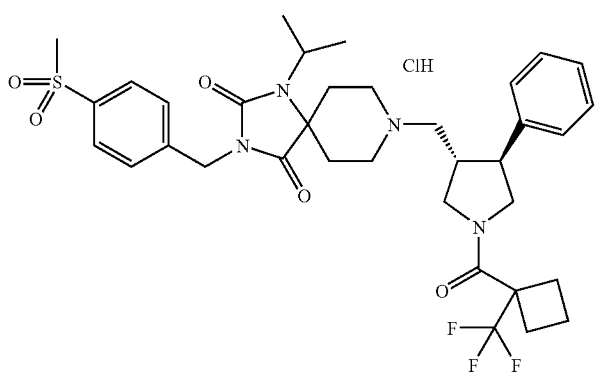 | | 1-Isopropyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride |
| 30 | 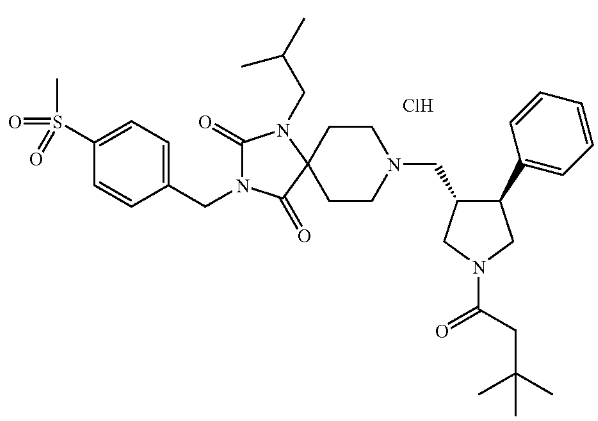 | | 8-[(3S,4S)-1-(3,3-Dimethyl-butyryl)-4-phenyl-pyrrolidin-3-ylmethyl]-1-isobutyl-3-(4-methanesulfonyl-benzyl)-1,3,8-triaza-spiro[4.5]decane-2,4-dione hydrochloride |

TABLE 1-continued

| CPD# | STRUCTURE | IC$_{50}$ HIV-1 PM1 | COMPOUND NAME |
|---|---|---|---|
| 31 | 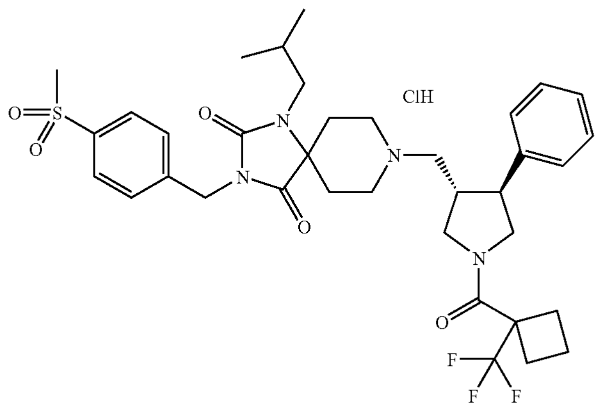 | | 1-Isobutyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride |
| 32 | 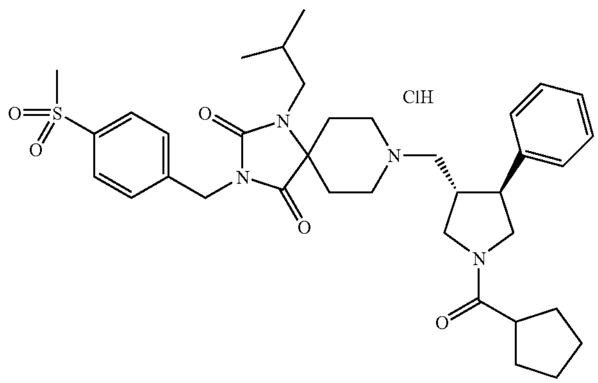 | | 8-((3S,4S)-1-Cyclopentanecarbonyl-4-phenyl-pyrrolidin-3-ylmethyl)-1-isobutyl-3-(4-methanesulfonyl-benzyl)-1,3,8-triaza-spiro[4.5]decane-2,4-dione hydrochloride |

EXAMPLE 6

General Procedures for Producing Compounds in Accordance with the Invention.

Example 6 describes hypothetical chemical procedure that could be used to obtain compounds in accordance with this invention. It is understood that a person skilled in the art can adapt the procedures described in this application to obtain the compounds of this invention.

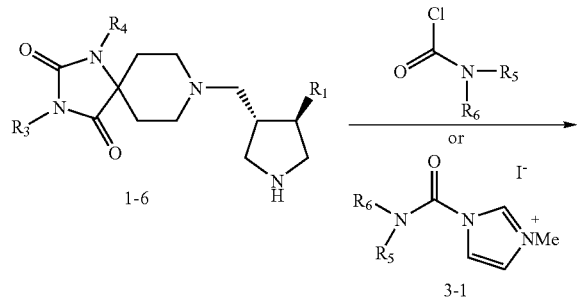

Scheme 4

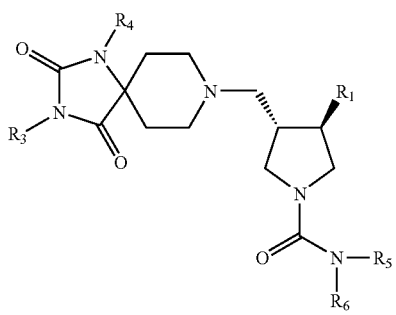

General procedure: the pyrrolidine 1-6 is submitted to reaction with isocyanate in solvent such as THF, or condensed with carbamoyl chloride derivative or with cationic carbamoyl imidazolium intermediate 3-1 (see R. A. Batey et al. *Comb. Chem. High Throughput Screening* 2002, 5, 219-232) in solvent such as DCM in presence of base such as triethylamine or diisopropylethylamine to provide the urea 3-2.

Scheme 5

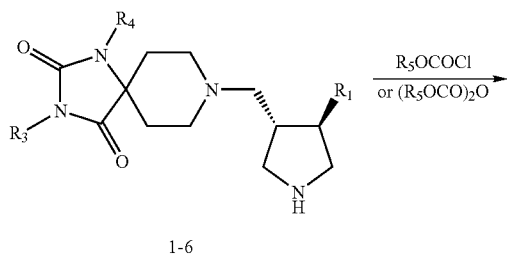

General procedure: the pyrrolidine 1-6 is condensed with chloroformate or symmetric anhydride in solvents such as DCM or 1,2-dichloroethane in the presence of a base such as triethylamine or diisopropylethylamine to provide the carbamate 4-1.

Scheme 6

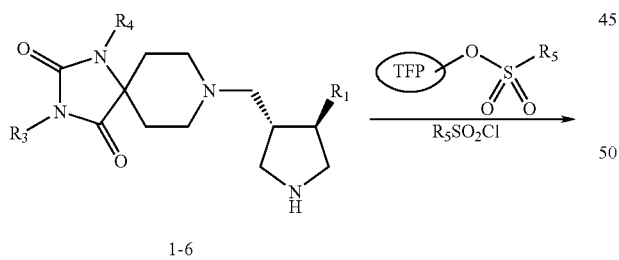

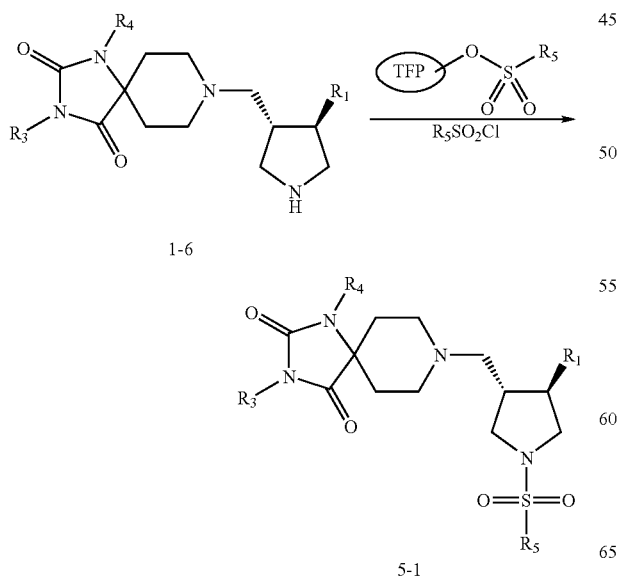

General procedure: the pyrrolidine 1-6 is condensed with preactivated sulfonyl chloride $R_5SO_2Cl$ on polymeric 4-hydroxy-2,3,5,6-tetrafluorobenzamido (TFP) resin (see reparation in J. M. Salvino et al. *J. Comb. Chem.* 2000, 2, 691-697) in solvent such as DMF, or with sulfonyl chloride $R_5SO_2Cl$ in solvent such as DCM in presence of a base such as triethylamine or diisopropylethylamine to provide the sulphonamide 5-1.

Scheme 7

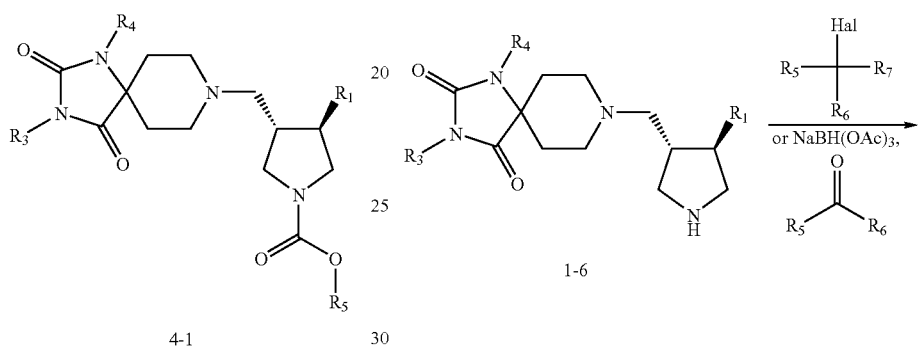

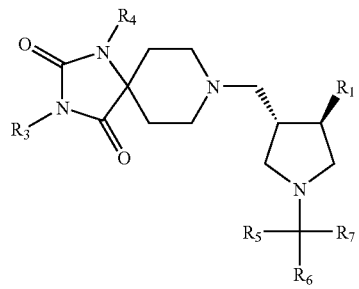

General procedure: the pyrrolidine 1-6 is reacted with halogenoalkyl derivative $R_5R_6R_7CHal$ in solvents such as DMF or DMA at temperature ranged from 25 to 100° C. using an inorganic base such as $Na_2CO_3$, $K_2CO_3$ or $Cs_2CO_3$, or condensed with aldehyde or ketone using conventional reductive amination reaction condition (see Abdel-Magid A. F. et al. *J. Org. Chem.* 1996, 61, 3849-3862) to provide the amine 6-1.

Table 2 of compounds illustrates some of the hypothetical compounds of the present invention which could be synthesized using the procedures described in schemes 3 to 7.

TABLE 2

| | STRUCTURE | COMPOUND NAME |
|---|---|---|
| 33 | 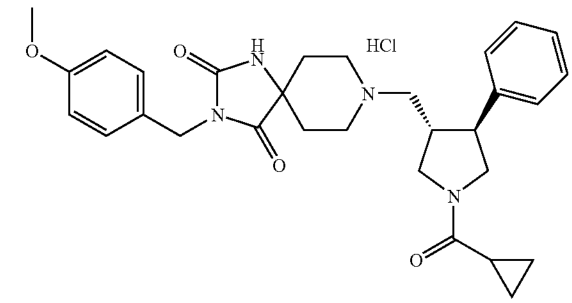 | 8-((3S,4S)-1-Cyclopropanecarbonyl-4-phenyl-pyrrolidin-3-ylmethyl)-3-(4-methoxy-benzyl)-1,3,8-triaza-spiro[4.5]decane-2,4-dione hydrochloride |
| 34 | 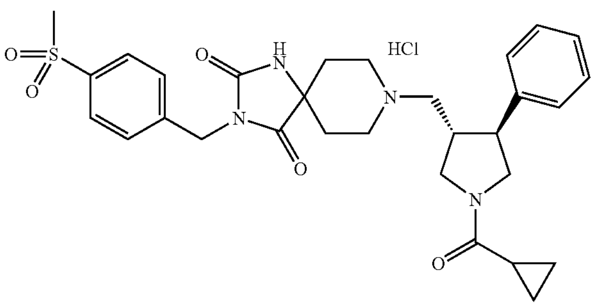 | 8-((3S,4S)-1-Cyclopropanecarbonyl-4-phenyl-pyrrolidin-3-ylmethyl)-3-(4-methanesulfonyl-benzyl)-1,3,8-triaza-spiro[4.5]decane-2,4-dione hydrochloride |
| 35 | 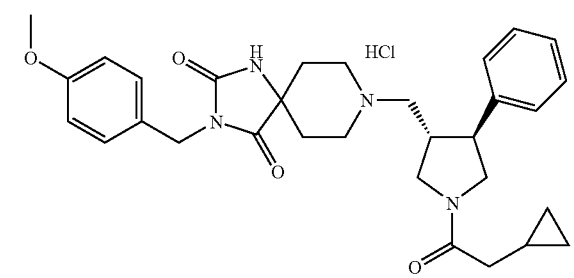 | 8-[(3S,4S)-1-(2-Cyclopropyl-acetyl)-4-phenyl-pyrrolidin-3-ylmethyl]-3-(4-methoxy-benzyl)-1,3,8-triaza-spiro[4.5]decane-2,4-dione hydrochloride |
| 36 | 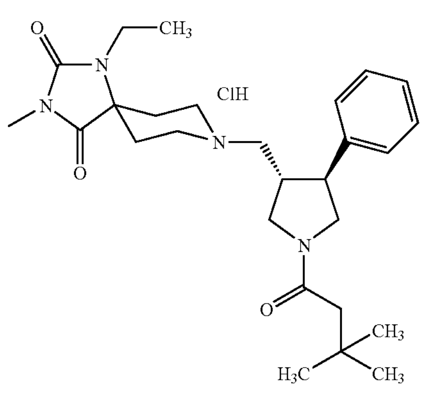 | 8-[(3S,4S)-1-(3,3-Dimethyl-butyryl)-4-phenyl-pyrrolidin-3-ylmethyl]-1-ethyl-3-methyl-1,3,8-triaza-spiro[4.5]decane-2,4-dione hydrochloride |

TABLE 2-continued

| | STRUCTURE | COMPOUND NAME |
|---|---|---|
| 37 | 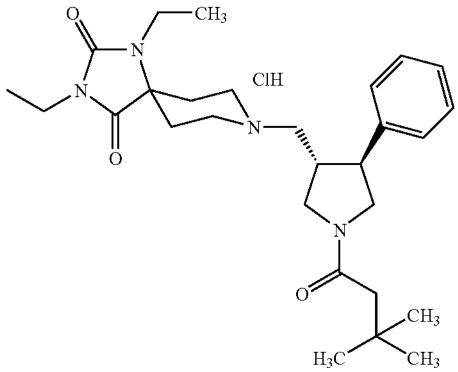 | 8-[(3S,4S)-1-(3,3-Dimethyl-butyryl)-4-phenyl-pyrrolidin-3-ylmethyl]-1,3-diethyl-1,3,8-triaza-spiro[4.5]decane-2,4-dione hydrochloride |
| 38 | 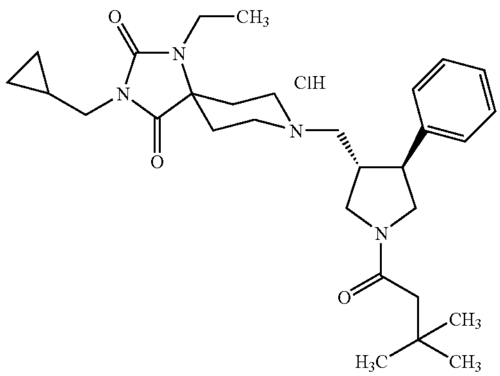 | 3-Cyclopropylmethyl-8-[(3S,4S)-1-(3,3-dimethyl-butyryl)-4-phenyl-pyrrolidin-3-ylmethyl]-1-ethyl-1,3,8-triaza-spiro[4.5]decane-2,4-dione hydrochloride |
| 39 | 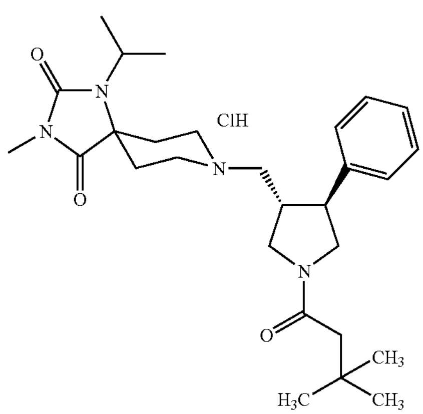 | 8-[(3S,4S)-1-(3,3-Dimethyl-butyryl)-4-phenyl-pyrrolidin-3-ylmethyl]-1-isopropyl-3-methyl-1,3,8-triaza-spiro[4.5]decane-2,4-dione hydrochloride |
| 40 | 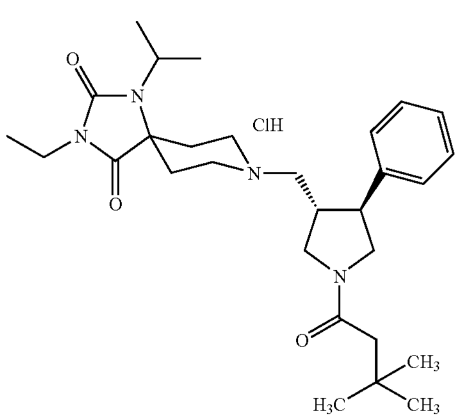 | 8-[(3S,4S)-1-(3,3-Dimethyl-butyryl)-4-phenyl-pyrrolidin-3-ylmethyl]-1-isopropyl-3-ethyl-1,3,8-triaza-spiro[4.5]decane-2,4-dione hydrochloride |

TABLE 2-continued

| STRUCTURE | COMPOUND NAME |
|---|---|
| 41 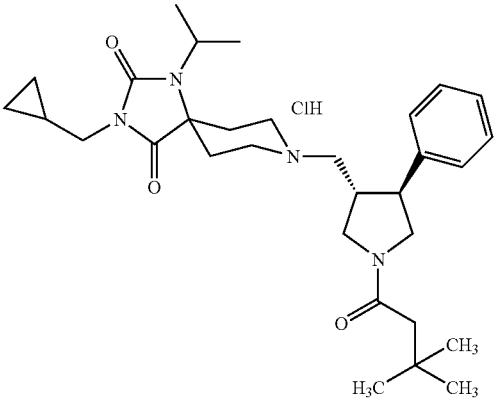 | 3-Cyclopropylmethyl-8-[(3S,4S)-1-(3,3-dimethyl-butyryl)-4-phenyl-pyrrolidin-3-ylmethyl]-1-isopropyl-1,3,8-triaza-spiro[4.5]decane-2,4-dione hydrochloride |
| 42 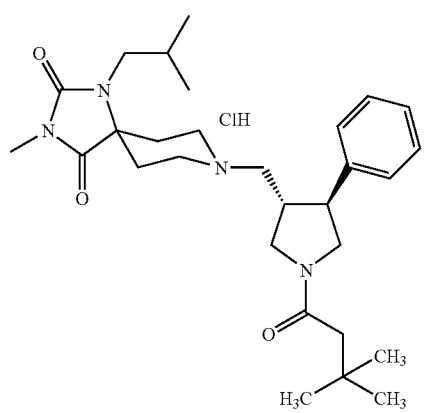 | 8-[(3S,4S)-1-(3,3-Dimethyl-butyryl)-4-phenyl-pyrrolidin-3-ylmethyl]-1-isobutyl-3-methyl-1,3,8-triaza-spiro[4.5]decane-2,4-dione hydrochloride |
| 43 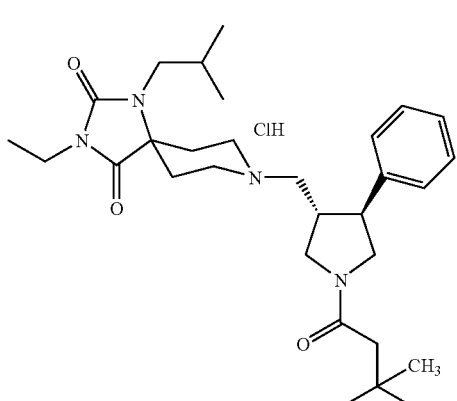 | 8-[(3S,4S)-1-(3,3-Dimethyl-butyryl)-4-phenyl-pyrrolidin-3-ylmethyl]-1-isobutyl-3-ethyl-1,3,8-triaza-spiro[4.5]decane-2,4-dione hydrochloride |

TABLE 2-continued

| | STRUCTURE | COMPOUND NAME |
|---|---|---|
| 44 | 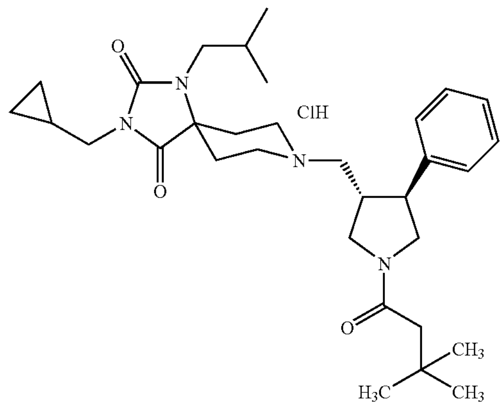 | 3-Cyclopropylmethyl-8-[(3S,4S)-1-(3,3-dimethyl-butyryl)-4-phenyl-pyrrolidin-3-ylmethyl]-1-isobutyl-1,3,8-triaza-spiro[4.5]decane-2,4-dione hydrochloride |
| 45 | 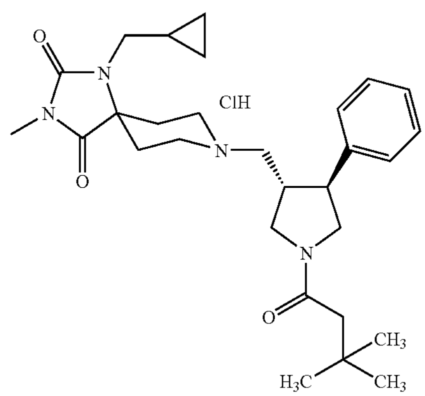 | 1-Cyclopropylmethyl-8-[(3S,4S)-1-(3,3-dimethyl-butyryl)-4-phenyl-pyrrolidin-3-ylmethyl]-3-methyl-1,3,8-triaza-spiro[4.5]decane-2,4-dione hydrochloride |
| 46 | 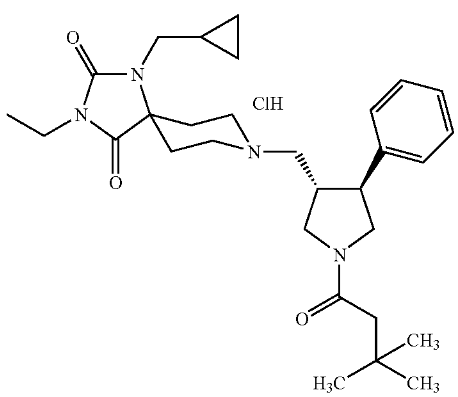 | 1-Cyclopropylmethyl-8-[(3S,4S)-1-(3,3-dimethyl-butyryl)-4-phenyl-pyrrolidin-3-ylmethyl]-3-ethyl-1,3,8-triaza-spiro[4.5]decane-2,4-dione hydrochloride |
| 47 | 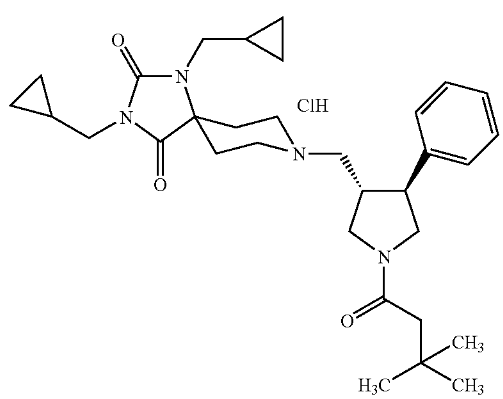 | 1,3-Bis-cyclopropylmethyl-8-[(3S,4S)-1-(3,3-dimethyl-butyryl)-4-phenyl-pyrrolidin-3-ylmethyl]-1,3,8-triaza-spiro[4.5]decane-2,4-dione hydrochloride |

TABLE 2-continued

| | STRUCTURE | COMPOUND NAME |
|---|---|---|
| 48 | 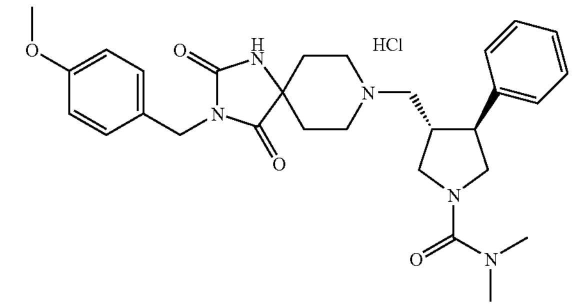 | (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid dimethylamide hydrochloride |
| 49 | 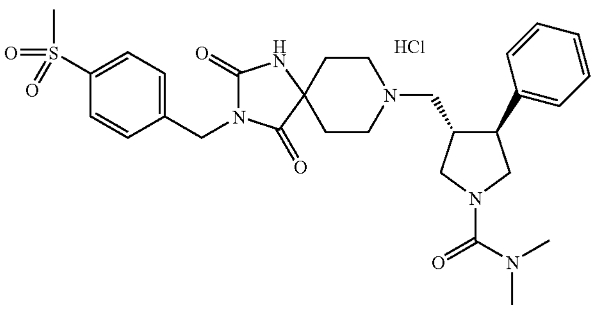 | (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid dimethylamide hydrochloride |
| 50 | 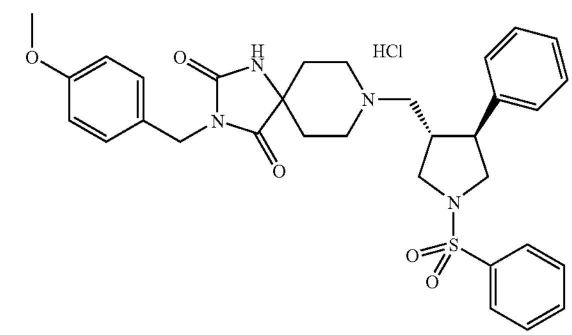 | 8-((3S,4S)-1-Benzenesulfonyl-4-phenyl-pyrrolidin-3-ylmethyl)-3-(4-methoxy-benzyl)-1,3,8-triaza-spiro[4.5]decane-2,4-dione hydrochloride |
| 51 | 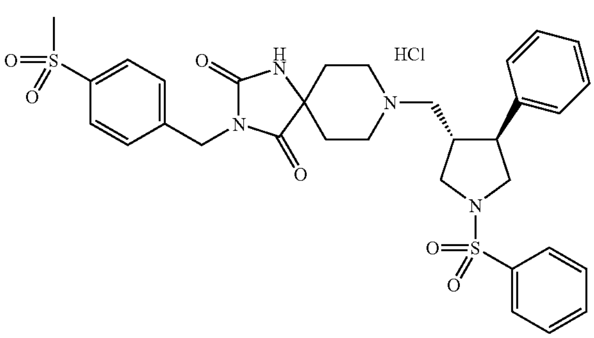 | 8-((3S,4S)-1-Benzenesulfonyl-4-phenyl-pyrrolidin-3-ylmethyl)-3-(4-methanesulfonyl-benzyl)-1,3,8-triaza-spiro[4.5]decane-2,4-dione hydrochloride |

TABLE 2-continued

| | STRUCTURE | COMPOUND NAME |
|---|---|---|
| 52 | 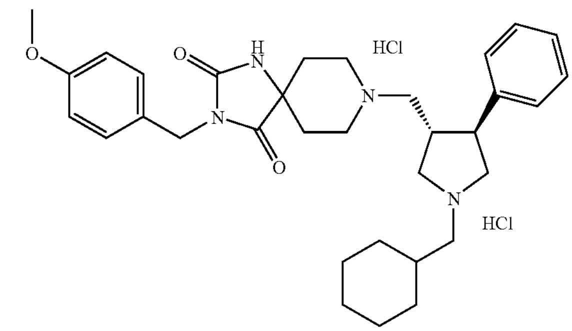 | 8-((3S,4S)-1-Cyclohexylmethyl-4-phenyl-pyrrolidin-3-ylmethyl)-3-(4-methoxy-benzyl)-1,3,8-triaza-spiro[4.5]decane-2,4-dione dihydrochloride |
| 53 | 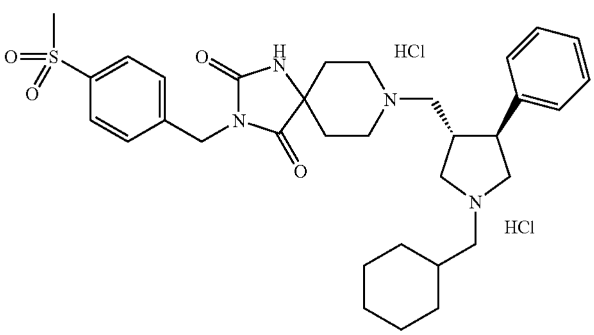 | 8-((3S,4S)-1-Cyclohexylmethyl-4-phenyl-pyrrolidin-3-ylmethyl)-3-(4-methanesulfonyl-benzyl)-1,3,8-triaza-spiro[4.5]decane-2,4-dione dihydrochloride |

The Following Assay Methods are Suitable for Evaluating the Compounds of the Invention.

A: Chemokine Binding Assay

Membranes (1 μg/well) from human embryonic kidney (HEK-293) cells expressing human CCR5 are incubated with 0.1 nM $^{125}$I-labeled MIP-1α (Amersham) in the presence of varying concentrations of a test compound (10000-0.01 nM) in buffer (50 mM Hepes, pH 7.3/5 mM $MgCl_2$/1 mM $CaCl_2$/0.5% BSA) for 90 min at room temperature. Reaction mixtures (100 μL) can be filtered through Multiscreen GFB filters (Millipore) and washed six times with cold wash buffer (50 mM Hepes, pH 7.3/0.5 M NaCl, 0.1% BSA). Bound $^{125}$I-MIP-1α can be quantitated by liquid scintillation counting. The nonspecific binding of $^{125}$I-labeled MIP-1α to the membrane can be determined based on the radioactivity from the wells added with 100 nM non-radiolabeled MIP-1α. $IC_{50}$ and $K_D$ values can be calculated by using GRAPHPAD PRISM software (Intuitive Software for Science, San Diego)

B: HIV-1 Replication in PBMC Cultures Assay

Isolated PBMC are stimulated in vitro with 5 μg/ml phytohemaglutinin and 50 units/ml IL-2 for 3 days. The cells are resuspended at $4 \times 10^6$/ml in complete medium (RPMI, 10% FBS/50 units/ml IL-2), seeded into 96-well plates ($2 \times 10^5$/well), incubated with inhibitor for 1 h at 37° C., and infected in triplicate with 25-100 tissue culture 50% infective dose ($TCID_{50}$) per well of the R5 HIV-1$_{JR-FL}$ strain for 3-4 h. The cells are washed twice in PBS to remove residual virus and cultured in the presence of inhibitor for 4-6 days. HIV-1 replication can be determined by the presence of viral RT activity in harvested supernatant fluid. The $IC_{50}$ values for the virus can be determined by using GRAPHPAD PRISM software.

C: HIV-1 Replication in PM1 Cell Culture Assay

Evaluation of the In Vitro Anti-HIV-1$_{Ba-L}$ Activity in PM1 Cell Line:

PM1 cell line which is a continuous CD4+ T-cell clone originally derived from a neoplastic T-cell line is used. PM1 is characterized by a unique susceptibility to a wide range of HIV-1 isolates, including primary and biologically pure macrophage-tropic isolates. Drugs are serially diluted (9 concentrations in duplicates) and added to wells of a flat bottom 96-well plate. PM1 cells are infected with HIV-1Ba-L at a multiplicity of infection of 0.5 for a period of 3 hours. Unbound viruses are removed by washing the cells two times through centrifugation followed by seeding the cells into a 96-well plate in the presence of the serially diluted test compounds with final concentrations ranging from 0.00256 to 5000 ηM. Thereafter, plates were incubated for a period of 6 days at 37° C. in a $CO_2$ incubator. Thereafter, culture supernatants are collected at day 6 and stored at −80° C. for viral quantification. The amount of virus present in cell culture supernatants is quantified using a reverse transcriptase assay. The concentration causing 50% inhibition of viral replication ($IC_{50}$) is calculated using Graph Pad Prism software.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A compound represented by formula (I):

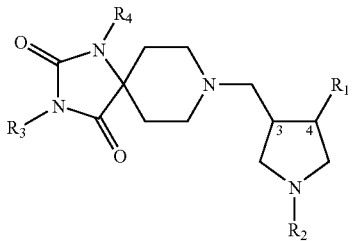

or a pharmaceutically acceptable salt thereof,
wherein $R_1$ is $C_{6-12}$ aryl optionally substituted by halogen, nitro, hydroxyl, $SO_3H$, $SO_{03}$—$C_{1-6}$ alkyl, $PO_3H_2$, $PO_3H$—$C_{1-6}$ alkyl, $PO_3H$—$C_{6-12}$ aryl, $PO_{03}(C_{1-6}$ alkyl$)_2$, $PO_{03}(C_{6-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$ aryl, $COOH$, $COO$—$C_{1-6}$ alkyl, $S$—$C_{1-6}$ alkyl, $O$—$C_{1-6}$ alkyl, $O$—$C_{2-6}$ alkenyl, $O$—$C_{2-6}$ alkynyl, amino, $NH$—$C_{1-6}$ alkyl, $NH$—$C_{6-12}$ aryl, $N(C_{1-6}$ alkyl$)_2$, and/or $N(C_{6-12}$ aryl$)_2$;

$R_2$ is H, $$\overset{O}{\underset{}{\cdots\!\!-\!\!C\!\!-\!\!R_5,}} \qquad (II)$$

$$\overset{O}{\underset{R_6}{\cdots\!\!-\!\!C\!\!-\!\!N\!\!-\!\!R_5,}} \qquad (III)$$

$$\overset{O}{\underset{}{\cdots\!\!-\!\!C\!\!-\!\!O\!\!-\!\!R_5,}} \qquad (IV)$$

$$\overset{O\;\;\;O}{\underset{}{\cdots\!\!-\!\!S\!\!-\!\!R_5,}}\text{ or} \qquad (V)$$

$$\cdots\!\!-\!\!\underset{R_7}{\overset{R_5}{\underset{|}{\overset{|}{C}}}}\!\!-\!\!R_6; \qquad (VI)$$

$R_3$ and $R_4$ are each independently H, $C_{1-10}$ alkyl, $C_{2-10}$ alkenyl, or $C_{2-10}$ alkynyl, which in each case is optionally substituted by halogen, nitro, hydroxyl, $SO_3H$, $SO_3$—$C_{1-6}$ alkyl, $PO_3H_2$, $PO_3H$—$C_{1-6}$ alkyl, $PO_3H$—$C_{6-12}$ aryl, $PO_3(C_{1-6}$ alkyl$)_2$, $PO_3(C_{6-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$ aryl, $COOH$, $COO$—$C_{1-6}$ alkyl, $S$—$C_{1-6}$ alkyl, $O$—$C_{1-6}$ alkyl, $O$—$C_{2-6}$ alkenyl, $O$—$C_{2-6}$ alkynyl, amino, $NH$—$C_{1-6}$ alkyl, $NH$—$C_{6-12}$ aryl, $N(C_{1-6}$ alkyl$)_2$, $N(C_{6-12}$ aryl$)_2$, and/or $C_{6-12}$ aryl, $C_{6-12}$ aryl optionally substituted by halogen, nitro, hydroxyl, $SO_3H$, $SO_3$—$C_{1-6}$ alkyl, $PO_3H_2$, $PO_3H$—$C_{1-6}$ alkyl, $PO_3H$—$C_{6-12}$ aryl, $PO_3(C_{1-6}$ alkyl$)_2$, $PO_3(C_{6-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$aryl, $COOH$, $COO$—$C_{1-6}$ alkyl, $S$—$C_{1-6}$ alkyl, $O$—$C_{1-6}$ alkyl, $O$—$C_{2-6}$ alkenyl, $O$—$C_{2-6}$ alkynyl, amino, $NH$—$C_{1-6}$ alkyl, $NH$—$C_{6-12}$ aryl, $N(C_{1-6}$ alkyl$)_2$, and/or $N(C_{6-12}$ aryl$)_2$, or $C_{7-12}$ aralkyl optionally substituted by halogen, nitro, hydroxyl, $SO_3H$, $SO_3$—$C_{1-6}$ alkyl, $PO_3H_2$, $PO_3H$—$C_{1-6}$ alkyl, $PO_3H$—$C_{6-12}$ aryl, $PO_3(C_{1-6}$ alkyl$)_2$, $PO_3(C_{6-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$ aryl, $COOH$, $COO$—$C_{1-6}$ alkyl, $S$—$C_{1-6}$ alkyl, $O$—$C_{1-6}$ alkyl, $O$—$C_{2-6}$ alkenyl, $O$—$C_{2-6}$ alkynyl, amino, $NH$—$C_{1-6}$ alkyl, $NH$—$C_{6-12}$ aryl, $N(C_{1-6}$ alkyl$)_2$, and/or $N(C_{6-12}$ aryl$)_2$;

$R_5$ is H, $C_{1-10}$ alkyl, $C_{2-10}$ alkenyl, or $C_{2-10}$ alkynyl, which in each case is optionally substituted by halogen, nitro, hydroxyl, $SO_3H$, $SO_3$—$C_{1-6}$ alkyl, $PO_3H_2$, $PO_3H$—$C_{1-6}$ alkyl, $PO_3H$—$C_{6-12}$ aryl, $PO_3(C_{1-6}$ alkyl$)_2$, $PO_3(C_{1-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$aryl, $COOH$ $COO$—$C_{1-6}$ alkyl, $S$—$C_{1-6}$ alkyl, $O$—$C_{1-6}$ alkyl, $O$—$C_{2-6}$ alkenyl, $O$—$C_{2-6}$ alkynyl, amino, $NH$—$C_{1-6}$ alkyl, $NH$—$C_{6-12}$ aryl, $N(C_{1-6}$ alkyl$)_2$, $N(C_{6-12}$ aryl$)_2$, and/or $C_{6-12}$ aryl, $C_{6-12}$ aryl optionally substituted by halogen, nitro, hydroxyl, $SO_3H$, $SO_3$—$C_{1-6}$ alkyl, $PO_3H_2$, $PO_3H$—$C_{1-6}$ alkyl, $PO_3H$—$C_{6-12}$ aryl, $PO_3(C_{1-6}$ alkyl$)_2$, $PO_3(C_{6-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$ aryl, $COOH$, $COO$—$C_{1-6}$ alkyl, $S$—$C_{1-6}$ alkyl, $O$—$C_{1-6}$ alkyl, $O$—$C_{2-6}$ alkenyl, $O$—$C_{2-6}$ alkynyl, amino, $NH$—$C_{1-6}$ alkyl, $NH$—$C_{6-12}$ aryl, $N(C_{1-6}$ alkyl$)_2$, and/or $N(C_{6-12}$ aryl$)_2$, or $C_{7-12}$ aralkyl optionally substituted by halogen, nitro, hydroxyl, $SO_3H$, $SO_3$—$C_{1-6}$ alkyl, $PO_3H_2$, $PO_3H$—$C_{1-6}$ alkyl, $PO_3H$—$C_{6-12}$ aryl, $PO_3(C_{1-6}$ alkyl$)_2$, $PO_3(C_{6-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$ aryl, $COOH$, $COO$—$C_{1-6}$ alkyl, $S$—$C_{1-6}$ alkyl, $O$—$C_{1-6}$ alkyl, $O$—$C_{2-6}$ alkenyl, $O$—$C_{2-6}$ alkynyl, amino, $NH$—$C_{1-6}$ alkyl, $NH$—$C_{6-12}$ aryl, $N(C_{1-6}$ alkyl$)_2$, and/or $N(C_{6-12}$ aryl$)_2$;

$R_6$ is H, or $C_{1-10}$ alkyl, $C_{2-10}$ alkenyl, or $C_{2-10}$ alkynyl, which in each case is optionally substituted by halogen, nitro, hydroxyl, $SO_3H$, $SO_3$—$C_{1-6}$ alkyl, $PO_3H_2$, $PO_3H$—$C_{1-6}$ alkyl, $PO_3H$—$C_{6-12}$ aryl, $PO_3(C_{1-6}$ alkyl$)_2$, $PO_3(C_{6-12}$ aryl$)_2$, $CONH_2$, $CONH$—$C_{1-6}$ alkyl, $CONH$—$C_{6-12}$ aryl, $CON(C_{1-6}$ alkyl$)_2$, $CON(C_{6-12}$ aryl$)_2$, $NHCO$—$C_{1-6}$ alkyl, $NHCO$—$C_{6-12}$ aryl, $COOH$, $COO$—$C_{1-6}$ alkyl, $S$—$C_{1-6}$ alkyl, $O$—$C_{1-6}$ alkyl, $O$—$C_{2-6}$ alkenyl, $O$—$C_{2-6}$ alkynyl, amino, $NH$—$C_{1-6}$ alkyl, $NH$—$C_{6-12}$ aryl, $N(C_{1-6}$ alkyl$)_2$, $N(C_{6-12}$ aryl$)_2$, and/or $C_{6-12}$ aryl; and Rhd 7 is H, or $C_{1-10}$ alkyl, $C_{2-10}$ alkenyl, or $C_{2-10}$ alkynyl, which in each case is optionally substituted by halogen, nitro, hydroxyl, SO$_3$H, SO$_3$—C$_{1-6}$ alkyl, PO$_3$H$_2$, PO$_3$H—C$_{1-6}$ alkyl, PO$_3$H—C$_{6-12}$ aryl, PO$_3$(C$_{1-6}$ alkyl)$_2$, PO$_3$(C$_{6-12}$ aryl)$_2$, CONH$_2$, CONH—C$_{1-6}$ alkyl, CONH—C$_{6-12}$ aryl, CON(C$_{1-6}$ alkyl)$_2$, CON(C$_{6-12}$ aryl)$_2$, NHCO—C$_{1-6}$ alkyl, NHCO—C$_{6-12}$ aryl, COOH, COO—C$_{1-6}$ alkyl, S—C$_{1-6}$ alkyl, O—C$_{1-6}$ alkyl, O—C$_{2-6}$ alkenyl, O—C$_{2-6}$ alkynyl, amino, NH—C$_{1-6}$ alkyl, NH—C$_{6-12}$ aryl, N(C$_{1-6}$ alkyl)$_2$, N(C$_{6-12}$ aryl)$_2$, and/or C$_{6-12}$ aryl.

2. A compound according to claim 1 wherein said compound is in the form of the (3R, 4R)-diastereomer.

3. A compound according to claim 1 wherein said compound is in the form of the (3S, 4R)-diastereomer.

4. A compound according to claim 1 wherein said compound is in the form of the (3R, 4S)-diastereomer.

5. A compound according to claim 1 wherein said compound is in the form of the (3S, 4S)-diastereomer.

6. A compound according to claim 1 wherein R$_1$ is optionally substituted phenyl.

7. A compound according to claim 1 wherein R$_1$ is unsubstituted phenyl or phenyl substituted by one or more substituent chosen from methyl, F, Cl and Br.

8. A compound according to claim 1 wherein R$_5$ is H, optionally substituted C$_{1-10}$ alkyl, optionally substituted C$_{6-12}$ aryl, or optionally substituted C$_{7-12}$ aralkyl.

9. A compound according to claim 1 wherein R$_5$ is H or optionally substituted C$_{1-6}$ alkyl.

10. A compound according to claim 1 wherein R$_5$ is unsubstituted C$_{1-6}$ alkyl or C$_{1-6}$ alkyl substituted by one or more substituent chosen from —OCH$_3$, F, Cl and Br.

11. A compound according to claim 1 wherein R$_5$ is methyl, ethyl, propyl, isopropyl, cyclopropyl, butyl, CH$_2$-tert-butyl, tert-butyl cyclobutyl, pentyl, cyclopentyl, hexyl, cyclohexyl, heptyl, cycloheptyl, CH$_2$-cyclopropyl, CH$_2$-cyclobutyl, CH$_2$-cyclopentyl, or CH$_2$-cyclohexyl.

12. A compound according to claim 1 wherein R$_5$ is optionally substituted C$_{6-12}$ aryl.

13. A compound according to claim 1 wherein R$_5$ is unsubstituted C$_{6-12}$ aryl or C$_{6-12}$ aryl substituted by one or more substituent chosen from —OCH$_3$, F, Cl and Br.

14. A compound according to claim 1 wherein R$_5$ is optionally substituted phenyl.

15. A compound according to claim 1 wherein R$_5$ is unsubstituted phenyl or phenyl substituted by one or more substituent chosen from —OCH$_3$, F, Cl and Br.

16. A compound according to claim 1 wherein R$_2$ is H,

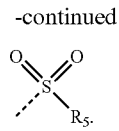

(II)

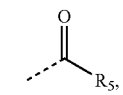

(III)

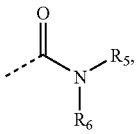

(IV)

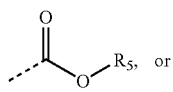

or

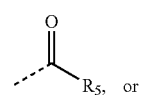

(V)

17. A compound according to claim 1 wherein R$_2$ is H,

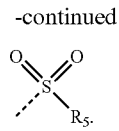

(II)

or

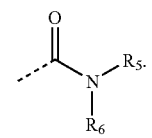

(III)

18. A compound according to claim 1 wherein R$_2$ is

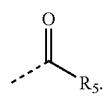

(II)

19. A compound according to claim 1 wherein R$_4$ is H, optionally substituted C$_{1-10}$ alkyl, optionally substituted C$_{2-10}$ alkenyl, or optionally substituted C$_{2-10}$ alkynyl.

20. A compound according to claim 1 wherein R$_4$ is H, or optionally substituted C$_{1-10}$ alkyl.

21. A compound according to claim 1 wherein R$_4$ is H, or optionally substituted C$_{1-6}$ alkyl.

22. A compound according to claim 1 wherein R$_4$ is H.

23. A compound according to claim 1 wherein R$_4$ is unsubstituted C$_{1-6}$ alkyl or C$_{1-6}$ alkyl substituted by one or more substituent chosen from OCH$_3$, F, Cl and Br.

24. A compound according to claim 1 wherein R$_4$ is methyl, ethyl, propyl, pentyl, cyclopentyl, hexyl, cyclohexyl, CH$_2$-cyclopropyl, CH$_2$-cyclobutyl, CH$_2$-cyclopentyl, or CH$_2$-cyclohexyl.

25. A compound according to claim 1 wherein R$_3$ is H, optionally substituted C$_{1-6}$ alkyl, optionally substituted C$_{2-6}$ alkenyl, optionally substituted C$_{2-6}$ alkynyl, optionally substituted C$_{6-12}$ aryl, or optionally substituted C$_{7-12}$ aralkyl.

26. A compound according to claim 1 wherein R$_3$ is H, or optionally substituted C$_{1-6}$ alkyl.

27. A compound according to claim 1 wherein R$_3$ is optionally substituted C$_{7-12}$ aralkyl.

28. A compound according to claim 1 wherein R$_3$ is optionally substituted benzyl.

29. A compound according to claim 1 wherein R$_3$ is unsubstituted benzyl or benzyl substituted by one or more substituent chosen from Br, F, Cl, C$_{1-3}$ alkoxy, SO$_2$C$_{1-3}$alkyl.

30. A compound according to claim 1 wherein R$_3$ is unsubstituted benzyl or benzyl substituted by one or more substituent chosen from Br, F, Cl, —OMe or methanesulfonyl.

31. A compound according to claim 1 wherein R$_3$ is benzyl substituted in the para position by one substituent chosen from Br, F, Cl, —OMe or methanesulfonyl.

32. A compound chosen from:

Compound 1 (3S,4S)-3-[3-(4-Bromo-benzyl)-2,4-dioxo-1,3,8-triaza-spiro[4.5]dec-8-ylmethyl]-4-phenyl-pyrrolidine-1-carboxylic acid tert-butyl ester;

Compound 2 (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid tert-butyl ester;

Compound 3 (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 4 (3S,4S)-3-[1-Ethyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 5 (3S,4S)-3-[1-Isopropyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 6 (3S,4S)-3-[1-Isobutyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 7 (3S,4S)-3-(1-Ethyl-2,4-dioxo-3-propyl-1,3,8-triaza-spiro[4.5]dec-8-ylmethyl)-4-phenyl-pyrrolidine-1-carboxylic acid tert-butyl ester;

Compound 8 3-(4-Bromo-benzyl)-8-((3R,4S)-4-phenyl-pyrrolidin-3-ylmethyl)-1,3,8-triaza-spiro[4.5]decane-2,4-dione;

Compound 9 3-(4-Methoxy-benzyl)-8-((3R,4S)-4-phenyl-pyrrolidin-3-ylmethyl)-1,3,8-triaza-spiro[4.5]decane-2,4-dione;

Compound 10 3-(4-Methanesulfonyl-benzyl)-8-((3R,4S)-4-phenyl-pyrrolidin-3-ylmethyl)-1,3,8-triaza-spiro[4.5]decane-2,4-dione;

Compound 11 1-Ethyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 12 1-Isopropyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 13 1-Isobutyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 14 1-Ethyl-8-((3R,4S)-4-phenyl-pyrrolidin-3-ylmethyl)-3-propyl-1,3,8-triaza-spiro[4.5]decane-2,4-dione;

Compound 15 3-(4-Methanesulfonyl-benzyl)-8-((3S,4S)-4-phenyl-1-propionyl-pyrrolidin-3-ylmethyl)-1,3,8-triaza-spiro[4.5]decane-2,4-dione;

Compound 16 3-(4-Methanesulfonyl-benzyl)-8-[(3S,4S)-1-methyl-cyclopropanecarbonyl)-4-phenyl-pyrrolidin-3-ylmethyl]-1,3,8-triaza-spiro[4.5]decane-2,4-dione;

Compound 17 8-[(3S,4S)-1-(2-Cyclopropyl-acetyl)-4-phenyl-pyrrolidin-3-ylmethyl]-3-(4-methanesulfonyl-benzyl)-1,3,8-triaza-spiro[4.5]decane-2,4-dione;

Compound 18 8-((3S,4S)-1-Cyclopentanecarbonyl-4-phenyl-pyrrolidin-3-ylmethyl)-3-(4-methanesulfonyl-benzyl)-1,3,8-triaza-spiro[4.5]decane-2,4-dione;

Compound 19 8-[(3S,4S)-1-(4,4-Difluoro-cyclohexanecarbonyl)-4-phenyl-pyrrolidin-3-ylmethyl]-3-(4-methanesulfonyl-benzyl)-1,3,8-triaza-spiro[4.5]decane-2,4-dione;

Compound 20 8-[(3S,4S)-1-(2-Fluoro-benzoyl)-4-phenyl-pyrrolidin-3-ylmethyl]-3-(4-methanesulfonyl-benzyl)-1,3,8-triaza-spiro[4.5]decane-2,4-dione;

Compound 21 8-[(3S,4S)-1-(2-Chloro-benzoyl)-4-phenyl-pyrrolidin-3-ylmethyl]-3-(4-methanesulfonyl-benzyl)-1,3,8-triaza-spiro[4.5]decane-2,4-dione;

Compound 22 4-{8-[(3S,4S)-1-(4,4-Difluoro-cyclohexanecarbonyl)-4-phenyl-pyrrolidin-3-ylmethyl]-2,4-dioxo-1,3,8-triaza-spiro[4.5]dec-3-ylmethyl}-N,N-dimethyl-benzenesulfonamide;

Compound 23 8-[(3S,4S)-1-(3,3-Dimethyl-butyryl)-4-phenyl-pyrrolidin-3-ylmethyl]-3-(4-methanesulfonyl-benzyl)-1,3,8-triaza-spiro[4.5]decane-2,4-dione;

Compound 24 8-[(3S,4S)-1-(3,3-Dimethyl-butyryl)-4-phenyl-pyrrolidin-3-ylmethyl]-1-ethyl-3-propyl-1,3,8-triaza-spiro[4.5]decane-2,4-dione;

Compound 25 8-[(3S,4S)-1-(3,3-Dimethyl-butyryl)-4-phenyl-pyrrolidin-3-ylmethyl]-1-ethyl-3-(4-methanesulfonyl-benzyl)-1,3,8-triaza-spiro[4.5]decane-2,4-dione;

Compound 26 1-Ethyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione;

Compound 27 8-((3S,4S)-1-Cyclopentanecarbonyl-4-phenyl-pyrrolidin-3-ylmethyl)-1-ethyl-3-(4-methanesulfonyl-benzyl)-1,3,8-triaza-spiro[4.5]decane-2,4-dione;

Compound 28 8-[(3S,4S)-1-(3,3-Dimethyl-butyryl)-4-phenyl-pyrrolidin-3-ylmethyl]-1-isopropyl-3-(4-methanesulfonyl-benzyl)-1,3,8-triaza-spiro[4.5]decane-2,4-dione;

Compound 29 1-Isopropyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione;

Compound 30 8-[(3S,4S)-1-(3,3-Dimethyl-butyryl)-4-phenyl-pyrrolidin-3-ylmethyl]-1-isobutyl-3-(4-methanesulfonyl-benzyl)-1,3,8-triaza-spiro[4.5]decane-2,4-dione;

Compound 31 1-Isobutyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione;

Compound 32 8-((3S,4S)-1-Cyclopentanecarbonyl-4-phenyl-pyrrolidin-3-ylmethyl)-1-isobutyl-3-(4-methanesulfonyl-benzyl)-1,3,8-triaza-spiro[4.5]decane-2,4-dione;

Compound 33 8-((3S,4S)-1-Cyclopropanecarbonyl-4-phenyl-pyrrolidin-3-ylmethyl)-3-(4-methoxy-benzyl)-1,3,8-triaza-spiro[4.5]decane-2,4-dione;

Compound 34 8-((3S,4S)-1-Cyclopropanecarbonyl-4-phenyl-pyrrolidin-3-ylmethyl)-3-(4-methanesulfonyl-benzyl)-1,3,8-triaza-spiro[4.5]decane-2,4-dione;

Compound 35 8-[(3S,4S)-1-(2-Cyclopropyl-acetyl)-4-phenyl-pyrrolidin-3-ylmethyl]-3-(4-methoxy-benzyl)-1,3,8-triaza-spiro[4.5]decane-2,4-dione;

Compound 36 8-[(3S,4S)-1-(3,3-Dimethyl-butyryl)-4-phenyl-pyrrolidin-3-ylmethyl]-1-ethyl-3-methyl-1,3,8-triaza-spiro[4.5]decane-2,4-dione;

Compound 37 8-[(3S,4S)-1-(3,3-Dimethyl-butyryl)-4-phenyl-pyrrolidin-3-ylmethyl]-1,3-diethyl-1,3,8-triaza-spiro[4.5]decane-2,4-dione;

Compound 38 3-Cyclopropylmethyl-8-[(3S,4S)-1-(3,3-dimethyl-butyryl)-4-phenyl-pyrrolidin-3-ylmethyl]-1-ethyl-1,3,8-triaza-spiro[4.5]decane-2,4-dione;

Compound 39 8-[(3S,4S)-1-(3,3-Dimethyl-butyryl)-4-phenyl-pyrrolidin-3-ylmethyl]-1-isopropyl-3-methyl-1,3,8-triaza-spiro[4.5]decane-2,4-dione;

Compound 40 8-[(3S,4S)-1-(3,3-Dimethyl-butyryl)-4-phenyl-pyrrolidin-3-ylmethyl]-1-isopropyl-3-ethyl-1,3,8-triaza-spiro[4.5]decane-2,4-dione;

Compound 41 3-Cyclopropylmethyl-8-[(3S,4S)-1-(3,3-dimethyl-butyryl)-4-phenyl-pyrrolidin-3-ylmethyl]-1-isopropyl-1,3,8-triaza-spiro[4.5]decane-2,4-dione;

Compound 42 8-[(3S,4S)-1-(3,3-Dimethyl-butyryl)-4-phenyl-pyrrolidin-3-ylmethyl]-1-isobutyl-3-methyl-1,3,8-triaza-spiro[4.5]decane-2,4-dione;

Compound 43 8-[(3S,4S)-1-(3,3-Dimethyl-butyryl)-4-phenyl-pyrrolidin-3-ylmethyl]-1-isobutyl-3-ethyl-1,3,8-triaza-spiro[4.5]decane-2,4-dione Compound 44 3-Cyclopropylmethyl-8-[(3S,4S)-1-(3,3-dimethyl-butyryl)-4-phenyl-pyrrolidin-3-ylmethyl]-1-isobutyl-1,3,8-triaza-spiro[4.5]decane-2,4-dione;

Compound 45 1-Cyclopropylmethyl-8-[(3S,4S)-1-(3,3-dimethyl-butyryl)-4-phenyl-pyrrolidin-3-ylmethyl]-3-methyl-1,3,8-triaza-spiro[4.5]decane-2,4-dione;

Compound 46 1-Cyclopropylmethyl-8-[(3S,4S)-1-(3,3-dimethyl-butyryl)-4-phenyl-pyrrolidin-3-ylmethyl]-3-ethyl-1,3,8-triaza-spiro[4.5]decane-2,4-dione;

Compound 47 1,3-Bis-cyclopropylmethyl-8-[(3S,4S)-1-(3,3-dimethyl-butyryl)-4-phenyl-pyrrolidin-3-ylmethyl]-1,3,8-triaza-spiro[4.5]decane-2,4-dione;

Compound 48 (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid dimethylamide;

Compound 49 (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid dimethylamide;

Compound 50 8-((3S,4S)-1-Benzenesulfonyl-4-phenyl-pyrrolidin-3-ylmethyl)-3-(4-methoxy-benzyl)-1,3,8-triaza-spiro[4.5]decane-2,4-dione;

Compound 51 8-((3S,4S)-1-Benzenesulfonyl-4-phenyl-pyrrolidin-3-ylmethyl)-3-(4-methanesulfonyl-benzyl)-1,3,8-triaza-spiro[4.5]decane-2,4-dione;

Compound 52 8-((3S,4S)-1-Cyclohexylmethyl-4-phenyl-pyrrolidin-3-ylmethyl)-3-(4-methoxy-benzyl)-1,3,8-triaza-spiro[4.5]decane-2,4-dione;

Compound 53 8-((3S,4S)-1-Cyclohexylmethyl-4-phenyl-pyrrolidin-3-ylmethyl)-3-(4-methanesulfonyl-benzyl)-1,3,8-triaza-spiro[4.5]decane-2,4-dione;

and pharmaceutically acceptable salts thereof.

33. A pharmaceutical formulation comprising a compound as defined in claim 32 with a pharmaceutically acceptable carrier or excipient.

34. A composition comprising a compound as defined in claim 1 with a pharmaceutically acceptable carrier or excipient.

35. A composition comprising a compound as defined in claim 1 with a pharmaceutically acceptable carrier or excipient and at least one further therapeutic agent.

36. A compound according to claim 1, wherein
$R_1$ is unsubstituted phenyl or phenyl substituted by one or more substituent chosen from methyl, F, Cl and Br;
$R_5$ is H, unsubstituted $C_{1-6}$ alkyl, or $C_{1-6}$ alkyl substituted by one or more substituent chosen from —$OCH_3$, F, Cl and Br;
$R_4$ is H, unsubstituted $C_{1-6}$ alkyl, or $C_{1-6}$ alkyl substituted by one or more substituent chosen from $OCH_3$, F, Cl and Br;
$R_3$ is unsubstituted $C_{1-6}$ alkyl, or $C_{1-6}$ alkyl substituted by one or more halogen, unsubstituted benzyl or benzyl substituted by one or more substituent chosen from Br, F, Cl, $C_{1-3}$ alkoxy, $SO_2C_{1-3}$ alkyl; and
$R_6$ and $R_7$ are each H.

37. A compound according to claim 17, wherein
$R_1$ is unsubstituted phenyl or phenyl substituted by one or more substituent chosen from methyl, F, Cl and Br;
$R_5$ is H, unsubstituted $C_{1-6}$ alkyl, or $C_{1-6}$ alkyl substituted by one or more substituent chosen from —$OCH_3$, F, Cl and Br;
$R_4$ is H, unsubstituted $C_{1-6}$ alkyl, or $C_{1-6}$ alkyl substituted by one or more substituent chosen from $OCH_3$, F, Cl and Br;
$R_3$ is unsubstituted $C_{1-6}$ alkyl, or $C_{1-6}$ alkyl substituted by one or more halogen, unsubstituted benzyl or benzyl substituted by one or more substituent chosen from Br, F, Cl, $C_{1-3}$ alkoxy, $SO_2C_{1-3}$ alkyl; and
$R_6$ is H.

38. A compound according to claim 32 selected from:

Compound 1 (3S,4S)-3-[3-(4-Bromo-benzyl)-2,4-dioxo-1,3,8-triaza-spiro[4.5]dec-8-ylmethyl]-4-phenyl-pyrrolidine-1-carboxylic acid tert-butyl ester;

Compound 2 (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid tert-butyl ester;

Compound 3 (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 4 (3S,4S)-3-[1-Ethyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 5 (3S,4S)-3-[1-Isopropyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 6 (3S,4S)-3-[1-Isobutyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 7 (3S,4S)-3-(1-Ethyl-2,4-dioxo-3-propyl-1,3,8-triaza-spiro[4.5]dec-8-ylmethyl)-4-phenyl-pyrrolidine-1-carboxylic acid tert-butyl ester;

Compound 8 3-(4-Bromo-benzyl)-8-((3R,4S)-4-phenyl-pyrrolidin-3-ylmethyl)-1,3,8-triaza-spiro[4.5]decane-2,4-dione;

Compound 9 3-(4-Methoxy-benzyl)-8-((3R,4S)-4-phenyl-pyrrolidin-3-ylmethyl)-1,3,8-triaza-spiro[4.5]decane-2,4-dione;

Compound 10 3-(4-Methanesulfonyl-benzyl)-8-((3R,4S)-4-phenyl-pyrrolidin-3-ylmethyl)-1,3,8-triaza-spiro[4.5]decane-2,4-dione;

Compound 11 1-Ethyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 12 1-Isopropyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 13 1-Isobutyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 14 1-Ethyl-8-((3R,4S)-4-phenyl-pyrrolidin-3-ylmethyl)-3-propyl-1,3,8-triaza-spiro[4.5]decane-2,4-dione;

Compound 15 3-(4-Methanesulfonyl-benzyl)-8-((3S,4S)-4-phenyl-1-propionyl-pyrrlidin-3-ylmethyl)-1,3,8-triaza-spiro[4.5]decane-2,4-dione hydrochloride;

Compound 16 3-(4-Methanesulfonyl-benzyl)-8-[(3S,4S)-1-(1-methyl-cyclopropanecarbonyl)-4-phenyl-pyrrolidin-3-ylmethyl]-1,3,8-triaza-spiro[4.5]decane-2,4-dione hydrochloride;

Compound 17 8-[(3S,4S)-1-(2-Cyclopropyl-acetyl)-4-phenyl-pyrrolidin-3-ylmethyl]-3-(4-methanesulfonyl-benzyl)-1,3,8-triaza-spiro[4.5]decane-2,4-dione hydrochloride;

Compound 18 8-((3S,4S)-1 -Cyclopentanecarbonyl-4-phenyl-pyrrolidin-3-ylmethyl)-3-(4-methanesulfonyl-benzyl)-1,3,8-triaza-spiro[4.5]decane-2,4-dione hydrochloride;

Compound 19 8-[(3S,4S)-1-(4,4-Difluoro-cyclohexanecarbonyl)-4-phenyl-pyrrolidin-3-ylmethyl]-3-(4-methanesulfonyl-benzyl)-1,3,8-triaza-spiro[4.5]decane-2,4-dione hydrochloride;

Compound 20 8-[(3S,4S)-1-(2-Fluoro-benzoyl)-4-phenyl-pyrrolidin-3-ylmethyl]-3-(4-methanesulfonyl-benzyl)-1,3,8-triaza-spiro[4.5]decane-2,4-dione hydrochloride;

Compound 21 8-[(3S,4S)-1-(2-Chloro-benzoyl)-4-phenyl-pyrrolidin-3-ylmethyl]-3-(4-methanesulfonyl-benzyl)-1,3,8-triaza-spiro[4.5]decane-2,4-dione hydrochloride;

Compound 22 4-{8-[(3S,4S)-1-(4,4-Difluoro-cyclohexanecarbonyl)-4-phenyl-pyrrolidin-3-ylmethyl]-2,4-dioxo-1,3,8-triaza-spiro[4.5]dec-3-ylmethyl}-N,N-dimethyl -benzenesulfonamide hydrochloride;

Compound 23 8-[(3S,4S)-1-(3,3-Dimethyl-butyryl)-4-phenyl-pyrrolidin-3-ylmethyl]-3-(4-methanesulfonyl-benzyl)-1,3,8-triaza-spiro[4.5]decane-2,4-dione hydrochloride;

Compound 24 8-[(3S,4S)-1-(3,3-Dimethyl-butyryl)-4-phenyl-pyrrolidin-3-ylmethyl]-1-ethyl-3-propyl-1,3,8-triaza-spiro[4.5]decane-2,4-dione hydrochloride;

Compound 25 8-[(3S,4S)-1-(3,3-Dimethyl-butyryl)-4-phenyl-pyrrolidin-3-ylmethyl]-1 -ethyl-3-(4-methanesulfonyl-benzyl)-1,3,8-triaza-spiro[4.5]decane-2,4-dione hydrochloride;

Compound 26 1-Ethyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride;

Compound 27 8-((3S,4S)-1-Cyclopentanecarbonyl-4-phenyl-pyrrolidin-3-ylmethyl)-1 -ethyl-3-(4-methanesulfonyl-benzyl)-1,3,8-triaza-spiro[4.5]decane-2,4-dione hydrochloride;

Compound 28 8-[(3S,4S)-1-(3,3-Dimethyl-butyryl)-4-phenyl-pyrrolidin-3-ylmethyl]-1-isopropyl-3-(4-methanesulfonyl-benzyl)-1,3,8-triaza-spiro[4.5]decane-2,4-dione hydrochloride;

Compound 29 1-Isopropyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride;

Compound 30 8-[(3S,4S)-1-(3,3-Dimethyl-butyryl)-4-phenyl-pyrrolidin-3-ylmethyl]-1-isobutyl-3-(4-methanesulfonyl-benzyl)-1,3,8-triaza-spiro[4.5]decane-2,4-dione hydrochloride;

Compound 31 1-Isobutyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride;

Compound 32 8-((3S,4S)-1-Cyclopentanecarbonyl-4-phenyl-pyrrolidin-3-ylmethyl)-1-isobutyl-3-(4-methanesulfonyl-benzyl)-1,3,8-triaza-spiro[4.5]decane-2,4-dione hydrochloride;

Compound 33 8-((3S,4S)-1 -Cyclopropanecarbonyl-4-phenyl-pyrrolidin-3-ylmethyl)-3-(4-methoxy-benzyl)-1,3,8-triaza-spiro[4.5]decane-2,4-dione hydrochloride;

Compound 34 8-((3S,4S)-1-Cyclopropanecarbonyl-4-phenyl-pyrrolidin-3-ylmethyl)-3-(4-methanesulfonyl-benzyl)-1,3,8-triaza-spiro[4.5]decane-2,4-dione hydrochloride;

Compound 35 8-[(3S,4S)-1-(2-Cyclopropyl-acetyl)-4-phenyl-pyrrolidin-3-ylmethyl]-3-(4-methoxy-benzyl)-1,3,8-triaza-spiro[4.5]decane-2,4-dione hydrochloride;

Compound 36 8-[(3S,4S)-1-(3,3-Dimethyl-butyryl)-4-phenyl-pyrrolidin-3-ylmethyl]-1-ethyl-3-methyl-1,3,8-triaza-spiro[4.5]decane-2,4-dione hydrochloride;

Compound 37 8-[(3S,4S)-1-(3,3-Dimethyl-butyryl)-4-phenyl-pyrrolidin-3-ylmethyl]-1,3-diethyl-1,3,8-triaza-spiro[4.5]decane-2,4-dione hydrochloride;

Compound 38 3-Cyclopropylmethyl-8-[(3S,4S)-1-(3,3-dimethyl-butyryl)-4-phenyl-pyrrolidin-3-ylmethyl]-1-ethyl-1,3,8-triaza-spiro[4.5]decane-2,4-dione hydrochloride;

Compound 39 8-[(3S,4S)-1-(3,3-Dimethyl-butyryl)-4-phenyl-pyrrolidin-3-ylmethyl]-1-isopropyl-3-methyl-1,3,8-triaza-spiro[4.5]decane-2,4-dione hydrochloride;

Compound 40 8-[(3S,4S)-1-(3,3-Dimethyl-butyryl)-4-phenyl-pyrrolidin-3-ylmethyl]-1-isopropyl-3-ethyl-1,3,8-triaza-spiro[4.5]decane-2,4-dione hydrochloride;

Compound 41 3-Cyclopropylmethyl-8-[(3S,4S)-1-(3,3-dimethyl-butyryl)-4-phenyl-pyrrolidin-3-ylmethyl]-1-isopropyl-1,3,8-triaza-spiro[4.5]decane-2,4-dione hydrochloride;

Compound 42 8-[(3S,4S)-1-(3,3-Dimethyl-butyryl)-4-phenyl-pyrrolidin-3-ylmethyl]-1-isobutyl-3-methyl-1,3,8-triaza-spiro[4.5]decane-2,4-dione hydrochloride;

Compound 43 8-[(3S,4S)-1-(3,3-Dimethyl-butyryl)-4-phenyl-pyrrolidin-3-ylmethyl]-1-isobutyl-3-ethyl-1,3,8-triaza-spiro[4.5]decane-2,4-dione hydrochloride Compound 44 3-Cyclopropylmethyl-8-[(3S,4S)-1-(3,3-dimethyl-butyryl)-4-phenyl-pyrrolidin-3-ylmethyl]-1-isobutyl-1,3,8-triaza-spiro[4.5]decane-2,4-dione hydrochloride;

Compound 45 1-Cyclopropylmethyl-8-[(3S,4S)-1-(3,3-dimethyl-butyryl)-4-phenyl-pyrrolidin-3-ylmethyl]-3-methyl-1,3,8-triaza-spiro[4.5]decane-2,4-dione hydrochloride;

Compound 46 1-Cyclopropylmethyl-8-[(3S,4S)-1-(3,3-dimethyl-butyryl)-4-phenyl-pyrrolidin-3-ylmethyl]-3-ethyl-1,3,8-triaza-spiro[4.5]decane-2,4-dione hydrochloride;

Compound 47 1,3-Bis-cyclopropylmethyl-8-[(3S,4S)-1-(3,3-dimethyl-butyryl)-4-phenyl-pyrrolidin-3-ylmethyl]-1,3,8-triaza-spiro[4.5]decane-2,4-dione hydrochloride;

Compound 48 (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid dimethylamide hydrochloride;

Compound 49 (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid dimethylamide hydrochloride;

Compound 50 8-((3S,4S)-1-Benzenesulfonyl-4-phenyl-pyrrolidin-3-ylmethyl)-3-(4-methoxy-benzyl)-1,3,8-triaza-spiro[4.5]decane-2,4-dione hydrochloride;

Compound 51 8-((3S,4S)-1-Benzenesulfonyl-4-phenyl-pyrrolidin-3-ylmethyl)-3-(4-methanesulfonyl-benzyl)-1,3,8-triaza-spiro[4.5]decane-2,4-dione hydrochloride;

Compound 52 8-((3S,4S)-1-Cyclohexylmethyl-4-phenyl-pyrrolidin-3-ylmethyl)-3-(4-methoxy-benzyl)-1,3,8-triaza-spiro[4.5]decane-2,4-dione dihydrochloride; and Compound 53 8-((3S,4S)-1-Cyclohexylmethyl-4-phenyl-pyrrolidin-3-ylmethyl)-3-(4-methanesulfonyl-benzyl)-1,3,8-triaza-spiro[4.5]decane-2,4-dione dihydrochioride.

39. A compound according to claim 32, wherein said compound is:

Compound 1 (3S,4S)-3-[3-(4-Bromo-benzyl)-2,4-dioxo-1,3,8-triaza-spiro[4.5]dec-8-ylmethyl]-4-phenyl-pyrrolidine-1-carboxylic acid tert-butyl ester;

Compound 2 (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid tert-butyl ester;

Compound 3 (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 4 (3S,4S)-3-[1-Ethyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 5 (3S,4S)-3-[1-Isopropyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester;

Compound 6 (3S,4S)-3-[1-Isobutyl-3-(4-methanesulfonyl-benzyl)-2,4-dioxo-1,3,8-triaza-spiro[4.5]dec-8-ylmethyl]-4-phenyl-pyrrolidine-1-carboxylic acid tert-butyl ester; or Compound 7 (3S,4S)-3-(1-Ethyl-2,4-dioxo-3-propyl-1,3,8-triaza-spiro[4.5]dec-8-ylmethyl)-4-phenyl-pyrrolidine-1-carboxylic acid tert-butyl ester.

40. A compound according to claim 32, wherein said compound is:

Compound 8 3-(4-Bromo-benzyl)-8-((3R,4S)-4-phenyl-pyrrolidin-3-ylmethyl)-1,3,8-triaza-spiro[4.5]decane-2,4-dione;

Compound 9 3-(4-Methoxy-benzyl)-8-((3R,4S)-4-phenyl-pyrrolidin-3-ylmethyl)-1,3,8-triaza-spiro[4.5]decane-2,4-dione;

Compound 10 3-(4-Methanesulfonyl-benzyl)-8-((3R,4S)-4-phenyl-pyrrolidin-3-ylmethyl)-1,3,8-triaza-spiro[4.5]decane-2,4-dione;

Compound 11 1-Ethyl-3-(4-methanesulfonyl-benzyl)-8-((3R,4S)-4-phenyl-pyrrolidin-3-ylmethyl)-1,3,8-triaza-spiro[4.5]decane-2,4-dione;

Compound 12 1-Isopropyl-3-(4-methanesulfonyl-benzyl)-8-((3R,4S)-4-phenyl-pyrrolidin-3-ylmethyl)-1,3,8-triaza-spiro[4.5]decane2,4-dione;

Compound 13 1-Isobutyl-3-(4-methanesulfonyl-benzyl)-8-((3R,4S)-4-phenyl-pyrrolidin-3-ylmethyl)-1,3,8-triaza-spiro[4.5]decane-2,4-dione; or Compound 14 1-Ethyl-8-((3R,4S)-4-phenyl-pyrrolidin-3-ylmethyl)-3-propyl-1,3,8-triaza-spiro[4.5]decane-2,4-dione.

41. A compound according to claim 32, wherein said compound is:

Compound 15 3-(4-Methanesulfonyl-benzyl)-8-((3S,4S)-4-phenyl-1-propionyl-pyrrolidin-3-ylmethyl)-1,3,8-triaza-spiro[4.5]decane-2,4-dione hydrochloride;

Compound 16 3-(4-Methanesulfonyl-benzyl)-8-[(3S,4S)-1-(1-methyl-cyclopropanecarbonyl)-4-phenyl-pyrrolidin-3-ylmethyl]-1,3,8-triaza-spiro[4.5]decane-2,4-dione hydrochloride;

Compound 17 8-[(3S,4S)-1-(2-Cyclopropyl-acetyl)-4-phenyl-pyrrolidin-3-ylmethyl]-3-(4-methanesulfonyl-benzyl)-1,3,8-triaza-spiro[4.5]decane-2,4-dione hydrochloride;

Compound 18 8-((3S,4S)-1-Cyclopentanecarbonyl-4-phenyl-pyrrolidin-3-ylmethyl)-3-(4-methanesulfonyl-benzyl)-1,3,8-triaza-spiro[4.5]decane-2,4-dione hydrochloride;

Compound 19 8-[(3S,4S)-1-(4,4-Difluoro-cyclohexanecarbonyl)-4-phenyl -pyrrolidin-3-ylmethyl]-3-(4-methanesulfonyl-benzyl)-1,3,8-triaza-spiro[4.5]decane-2,4-dione hydrochloride;

Compound 20 8-[(3S,4S)-1-(2-Fluoro-benzoyl)-4-phenyl-pyrrolidin-3-ylmethyl]-3-(4-methanesulfonyl-benzyl)-1,3,8-triaza-spiro[4.5]decane-2,4-dione hydrochloride;

Compound 21 8-[(3S,4S)-1-(2-Chloro-benzoyl)-4-phenyl-pyrrolidin-3-ylmethyl]-3-(4-methanesulfonyl-benzyl)-1,3,8-triaza-spiro[4.5]decane-2,4-dione hydrochloride;

Compound 22 4-{8-[(3S,4S)-1-(4,4-Difluoro-cyclohexanecarbonyl)-4-phenyl-pyrrolidin-3-ylmethyl]-2,4-dioxo-1,3,8-triaza-spiro[4.5]dec-3-ylmethyl}-N,N-dimethyl -benzenesulfonamide hydrochloride;

Compound 23 8-[(3S,4S)-1-(3,3-Dimethyl-butyryl)-4-phenyl-pyrrolidin-3-ylmethyl]-3-(4-methanesulfonyl-benzyl)-1,3,8-triaza-spiro[4.5]decane-2,4-dione hydrochloride;

Compound 34 8-((3S,4S)-1-Cyclopropanecarbonyl-4-phenyl-pyrrolidin-3-ylmethyl)-3-(4-methanesulfonyl-benzyl)-1,3,8-triaza-spiro[4.5]decane-2,4-dione hydrochloride;

Compound 49 (3S,4S)-3-[3-(4-Methanesulfonyl-benzyl)-2,4-dioxo-1,3,8-triaza-spiro[4.5]dec-8-ylmethyl]-4-phenyl-pyrrolidine-1-carboxylic acid dimethylamide hydrochloride;

Compound 51 8-((3S,4S)-1-Benzenesulfonyl-4-phenyl-pyrrolidin-3-ylmethyl)-3-(4-methanesulfonyl-benzyl)-1,3,8-triaza-spiro[4.5]decane-2,4-dione hydrochloride; or Compound 53 8-((3S,4S)-1-Cyclohexylmethyl-4-phenyl-pyrrolidin-3-ylmethyl)-3-(4-methanesulfonyl-benzyl)-1,3,8-triaza-spiro[4.5]decane-2,4-dione dihydrochloride.

42. A compound according to claim 32, wherein said compound is:

Compound 24 8-[(3S,4S)-1-(3,3-Dimethyl-butyryl)-4-phenyl-pyrrolidin-3-ylmethyl]-1-ethyl-3-propyl-1,3,8-triaza-spiro[4.5]decane-2,4-dione hydrochloride;

Compound 25 8-[(3S,4S)-1-(3,3-Dimethyl-butyryl)-4-phenyl-pyrrolidin-3-ylmethyl]-1-ethyl-3-(4-methanesulfonyl-benzyl)-1,3,8-triaza-spiro[4.5]decane-2,4-dione hydrochloride;

Compound 26 1-Ethyl-3-(4-methanesulfonyl-benzyl)-8-[(3S,4S)-4-phenyl -1-(1-trifluoromethyl-cyclobutanecarbonyl)-pyrrolidin-3-ylmethyl]-1,3,8-triaza-spiro[4.5]decane-2,4-dione hydrochloride;

Compound 27 8-((3S,4S)-1-Cyclopentanecarbonyl-4-phenyl-pyrrolidin-3-ylmethyl)-1-ethyl-3-(4-methanesulfonyl-benzyl)-1,3,8-triaza-spiro[4.5]decane-2,4-dione hydrochloride;

Compound 28 8-[(3S,4S)-1-(3,3-Dimethyl-butyryl)-4-phenyl-pyrrolidin-3-ylmethyl]-1-isopropyl-3-(4-methanesulfonyl-benzyl)-1,3,8-triaza-spiro[4.5]decane-2,4-dione hydrochloride;

Compound 29 1-Isopropyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride;

Compound 30 8-[(3S,4S)-1-(3,3-Dimethyl-butyryl)-4-phenyl-pyrrolidin-3-ylmethyl]-1-isobutyl-3-(4-methanesulfonyl-benzyl)-1,3,8-triaza-spiro[4.5]decane-2,4-dione hydrochloride;

Compound 31 1-Isobutyl-3-(4-methanesulfonyl-benzyl)-8-[(3S,4S)-4-phenyl-1-(1-trifluoromethyl-cyclobutanecarbonyl)-pyrrolidin-3-ylmethyl]-1,3,8-triaza-spiro[4.5]decane-2,4-dione hydrochloride; or Compound 32 8-((3S,4S)-1-Cyclopentanecarbonyl-4-phenyl-pyrrolidin-3-ylmethyl)-1-isobutyl-3-(4-methanesulfonyl-benzyl)-1,3,8-triaza-spiro[4.5]decane-2,4-dione hydrochloride.

43. A compound according to claim 32, wherein said compound is:

Compound 33 8-((3S,4S)-1-Cyclopropanecarbonyl-4-phenyl-pyrrolidin-3-ylmethyl)-3-(4-methoxy-benzyl)-1,3,8-triaza-spiro[4.5]decane-2,4-dione hydrochloride;

Compound 35 8-[(3S,4S)-1-(2-Cyclopropyl-acetyl)-4-phenyl-pyrrolidin-3-ylmethyl]-3-(4-methoxy-benzyl)-1,3,8-triaza-spiro[4.5]decane-2,4-dione hydrochloride;

Compound 48 (3S,4S)-3-[3-(4-Methoxy-benzyl)-2,4-dioxo-1,3,8-triaza-spiro[4.5]dec-8-ylmethyl]-4-phenyl-pyrrolidine-1-carboxylic acid dimethylamide hydrochloride;

Compound 50 8-((3S,4S)-1-Benzenesulfonyl-4-phenyl-pyrrolidin-3-ylmethyl)-3-(4-methoxy-benzyl)-1,3,8-triaza-spiro[4.5]decane-2,4-dione hydrochloride; or Compound 52 8-((3S,4S)-1-Cyclohexylmethyl-4-phenyl-pyrrolidin-3-ylmethyl)-3-(4-methoxy-benzyl)-1,3,8-triaza-spiro[4.5]decane-2,4-dione dihydrochloride.

44. A compound according to claim 32, wherein said compound is:

Compound 36 8-[(3S,4S)-1-(3,3-Dimethyl-butyryl)-4-phenyl-pyrrolidin-3-ylmethyl]-1-ethyl-3-methyl-1,3,8-triaza-spiro[4.5]decane-2,4-dione hydrochloride;

Compound 37 8-[(3S,4S)-1-(3,3-Dimethyl-butyryl)-4-phenyl-pyrrolidin-3-ylmethyl]-1,3-diethyl-1,3,8-triaza-spiro[4.5]decane-2,4-dione hydrochloride;

Compound 38 3-Cyclopropylmethyl-8-[(3S,4S)-1-(3,3-dimethyl-butyryl)-4-phenyl-pyrrolidin-3-ylmethyl]-1-ethyl-1,3,8-triaza-spiro[4.5]decane-2,4-dione hydrochloride;

Compound 39 8-[(3S,4S)-1-(3,3-Dimethyl-butyryl)-4-phenyl-pyrrolidin-3-ylmethyl]-1-isopropyl-3-methyl-1,3,8-triaza-spiro[4.5]decane-2,4-dione hydrochloride;

Compound 40 8-[(3S,4S)-1-(3,3-Dimethyl-butyryl)-4-phenyl-pyrrolidin-3-ylmethyl]-1-isopropyl-3-ethyl-1,3,8-triaza-spiro[4.5]decane-2,4-dione hydrochloride;

Compound 41 3-Cyclopropylmethyl-8-[(3S,4S)-1-(3,3-dimethyl-butyryl)-4-phenyl-pyrrolidin-3-ylmethyl]-1-isopropyl-1,3,8-triaza-spiro[4.5]decane-2,4-dione hydrochloride;

Compound 42 8-[(3S,4S)-1-(3,3-Dimethyl-butyryl)-4-phenyl-pyrrolidin-3-ylmethyl]-1-isobutyl-3-methyl-1,3,8-triaza-spiro[4.5]decane-2,4-dione hydrochloride;

Compound 43 8-[(3S,4S)-1-(3,3-Dimethyl-butyryl)-4-phenyl-pyrrolidin-3-ylmethyl]-1-isobutyl-3-ethyl-1,3,8-triaza-spiro[4.5]decane-2,4-dione hydrochloride Compound 44 3-Cyclopropylmethyl-8-[(3S,4S)-1-(3,3-dimethyl-butyryl)-4-phenyl-pyrrolidin-3-ylmethyl]-1-isobutyl-1,3,8-triaza-spiro[4.5]decane-2,4-dione hydrochloride;

Compound 45 1-Cyclopropylmethyl-8-[(3S,4S)-1-(3,3-dimethyl-butyryl)-4-phenyl-pyrrolidin-3-ylmethyl]-3-methyl-1,3,8-triaza-spiro[4.5]decane-2,4-dione hydrochloride;

Compound 46 1-Cyclopropylmethyl-8-[(3S,4S)-1-(3,3-dimethyl-butyryl)-4-phenyl-pyrrolidin-3-ylmethyl]-3-ethyl-1,3,8-triaza-spiro[4.5]decane-2,4-dione hydrochloride; or Compound 47 1,3-Bis-cyclopropylmethyl-8-[(3S,4S)-1-(3,3-dimethyl-butyryl)-4-phenyl-pyrrolidin-3-ylmethyl]-1,3,8-triaza-spiro[4.5]decane-2,4-dione hydrochloride.

* * * * *

UNITED STATES PATENT AND TRADEMARK OFFICE
CERTIFICATE OF CORRECTION

PATENT NO. : 7,709,642 B2  
APPLICATION NO. : 11/159406  
DATED : May 4, 2010  
INVENTOR(S) : Laval Chan Chun Kong et al.

Page 1 of 1

It is certified that error appears in the above-identified patent and that said Letters Patent is hereby corrected as shown below:

Column 59, line 20 reads: "hydroxyl, $SO_3H$, $SO_{03}$-$C_{1-6}$ alkyl, $PO_3H_2$, $PO_3H$-"  
Should read: -- hydroxyl, $SO_3H$, $SO_3$-$C_{1-6}$ alkyl, $PO_3H_2$, $PO_3H$— --

Column 59, line 21 reads: "$C_{1-6}$ alkyl, $PO_3$-$C_{6-12}$ aryl, $PO_{03}(C_{1-6}$ alkyl$)_2$, $PO_{03}$"  
Should read: -- $C_{1-6}$ alkyl, $PO_3$-$C_{6-12}$ aryl, $PO_3(C_{1-6}$ alkyl$)_2$, $PO_3$— --

Column 60, line 65 reads: "Rhd 7    is H, or"  
Should read: -- $R_7$    is H, or --

Column 66, line 62 reads: "4-phenyl-1-propionyl-pyrrlidin-3-ylmethyl)-1,3,8-"  
Should read: -- 4-phenyl-1-propionyl-pyrrolidin-3-ylmethyl)-1,3,8— --

Signed and Sealed this

Fifteenth Day of February, 2011

David J. Kappos  
*Director of the United States Patent and Trademark Office*